US007727952B2

(12) United States Patent
Sobue et al.

(10) Patent No.: US 7,727,952 B2
(45) Date of Patent: Jun. 1, 2010

(54) METHODS FOR TREATING SPINAL AND BULBAR MUSCULAR ATROPHY USING LHRH ANALOGS

(75) Inventors: Gen Sobue, Nagoya (JP); Masahisa Katsuno, Nagoya (JP); Hiroaki Adachi, Nagoya (JP)

(73) Assignee: Nagoya Industrial Science Research Institute, Nagoya-shi (JP)

( * ) Notice: Subject to any disclaimer, the term of this patent is extended or adjusted under 35 U.S.C. 154(b) by 628 days.

(21) Appl. No.: 11/518,209

(22) Filed: Sep. 11, 2006

(65) Prior Publication Data

US 2008/0182775 A1 Jul. 31, 2008

Related U.S. Application Data

(62) Division of application No. 10/524,823, filed on Feb. 18, 2005, now abandoned.

(30) Foreign Application Priority Data

Aug. 19, 2002 (JP) .............................. 2002-238599

(51) Int. Cl.
*A61K 38/09* (2006.01)
*A61K 38/24* (2006.01)
(52) U.S. Cl. .......................................... 514/2; 530/313
(58) Field of Classification Search ...................... None
See application file for complete search history.

(56) References Cited

U.S. PATENT DOCUMENTS

| 5,733,565 | A | * | 3/1998 | Moo-Young et al. | ......... | 424/424 |
| 6,096,764 | A | * | 8/2000 | Bryant et al. | ............... | 514/324 |
| 6,506,410 | B1 | | 1/2003 | Park et al. | .................... | 424/489 |
| 2004/0087557 | A1 | * | 5/2004 | Steiner et al. | ............... | 514/114 |

OTHER PUBLICATIONS

M. Katsuno, et al.; "Testosterone reduction prevents phenotypic expression in a transgenic mouse model of spinal and bulbar muscular atrophy;" *Neuron*; vol. 35; No. 5; Aug. 2002; pp. 843-854.
H. Adachi, et al.; "Transgenic mouse model of spinal and bulbar muscular atrophy;" *Society for Neuroscience Abstract Viewer and Itinerary Planner;* 2002; Abstract, No. 597.15.
R.S. Darrington, et al; "Protective effects of estrogens on polyglutamine-expanded androgen receptor aggregation in mice;" *Neurosci. Lett.;* No. 1; p. 350; Oct. 2003; pp. 37-40.
M. Katsuno, et al; Leuprorelin rescues polyglutamine-dependent phenotypes in a transgenic mouse model of spinal and bulbar muscular atrophy; *Nat.Med.*; vol. 9; No. 6; 2003; p. 768-773.
A. Abel, et al; "Expression of expanded repeat androgen receptor produces neurologic disease in trans genic mice;" *Hum. Mol. Genet.*; vol. 10; No. 2; Jan. 2001; pp. 107-116.
A.Abel et al., "Expression of expanded repeat androgen receptor produces neurologic disease in transgenic mice," *Human Molecular Genetics*, vol. 10, No. 2, 2001, pp. 107-116.

H. Adachi et al., "Transgenic mice with an expanded CAG repeat controlled by the human AR promoter show polyglutamine nuclear inclusions and neuronal dysfunction without neuronal cell death," *Human Molecular Genetics*, vol. 10, No. 10,2001, pp. 1039-1048.
O. A Andreassen et al., "Creatine Increases Survival and Delays Motor Symptoms in a Transgenic Animal Model of Huntington's Disease," *Neurobiology of Disease* 8,2001, pp. 479-491.
P. M. Bingham et al., "Stability of an expanded trinucleotide repeat in the androgen receptor gene in transgenic mice," *Nature Genetics*, vol. 9, Feb. 1995, pp. 191-196.
N. L. Chamberlain et al., "The length and location of CAG trinucleotide repeats in the androgen receptor N-terminal domain affect transactivation function," *Nucleic Acids Research*, vol. 22, No. 15, 1994, pp. 3181-3186.
C. J. Cummings et al., "Chaperone suppression of aggregation and altered subcellular proteasome localization imply protein misfolding in SCA 1," *Nature Genetics*, vol. 19, Jun. 1998, pp. 148-154.
C. J. Cummings et al., "Mutation of the E6-AP Ubiquitin Ligase Reduces Nuclear Inclusion Frequency While Accelerating Polyglutamine-Induced Pathology in *SCA 1* Mice," *Neuron*, vol. 24, Dec. 1999, pp. 879-892.
C. J. Cummings et al., "Over-expression of inducible HSP70 chaperone suppresses neuropathology and improves motor function in *SCA 1* mice," *Human Molecular Genetics*, vol. 10, No. 14, 2001, pp. 1511-1518.
A. Danek et al., "Decrease in androgen binding and effect of androgen treatment in a case of X-linked bulbospinal neuronopathy," *Clin Investig*, 72, 1994, pp. 892-897.
M. Doyu et al., "Severity of X-Linked Recessive Bulbospinal Neuronopathy Correlates with Size of the Tandem CAG Repeat in Androgen Receptor Gene," *Annals of Neurology*, vol. 32, No. 5, Nov. 1992, pp. 707-710.
M. Duyao et al, "Trinucleotide repeat length instability and age of onset in Huntington's disease," *Nature Genetics*, vol. 4, Aug. 1993, pp. 387-392.

(Continued)

*Primary Examiner*—Elizabeth C. Kemmerer
*Assistant Examiner*—Kimberly A. Ballard
(74) *Attorney, Agent, or Firm*—Edwards Angell Palmer & Dodge LLP

(57) ABSTRACT

It is intended to provide a model animal faithfully reproducing the pathogenic conditions of spinal and bulbar muscular atrophy, a method of screening a remedy for polyglutamine disease using the same, and a remedy for spinal and bulbar muscular atrophy. Namely, a nonhuman animal having the following characteristics (1) to (5) in its conditions or pathological findings: (1) showing progressive myoatrophy; (2) showing lowering in muscular power; (3) in immunostaining with the use of an anti-polyglutamine antibody, showing nuclear diffuse staining and nuclear inclusions; (4) in immunostaining with the use of an anti-androgen receptor antibody, showing nuclear diffuse staining and nuclear inclusions; and (5) showing a neurogenic change. A remedy for polyglutamine disease is screened by administering a test substance to this nonhuman animal and examining changes in its conditions or pathological findings. A remedy for spinal and bulbar muscular atrophy is prepared by using as the active ingredient a compound having an effect of inhibiting the secretion of testosterone.

6 Claims, 9 Drawing Sheets

OTHER PUBLICATIONS

J. N. Goldenberg et al, "Testosterone therapy and the pathogenesis of Kennedy's disease (X-linked bulbospinal muscular atrophy)," *Journal of the Neurological Sciences* 135, 1996, pp. 158-161.

C.-A. Gutekunst et al., "Nuclear and Neuropil Aggregates in Huntington's Disease: Relationship to Neuropathology," *Journal of Neuroscience* 19(7), Apr. 1999, pp. 2522-2534.

M. C. Hall et al., "Prospective Determination of the Hormonal Response After Cessation of Luteinizing Hormone-Releasing Hormone Agonist Treatment in Patients With Prostate Cancer," *Urology* 53(5), 1999, pp. 898-902.

V. Heiser et al., "Inhibition of Huntingtin Fibrillogenesis by Specific Antibodies and Small Molecules: Implications for Huntington's Disease Therapy," *Proceedings of the National Academy of Sciences of the United States of America*, vol. 97, No. 12, Jun. 2000, pp. 6739-6744.

D. P. Huynh et al., "Nuclear localization or inclusion body formation of ataxin-2 are not necessary for SCA2 pathogenesis in mouse or human," *Nature Genetics*, vol. 26, Sep. 2000, pp. 44-50.

S. Igarashi et al., "Strong correlation between the number of CAG repeats in androgen receptor genes and the clinical onset of features of spinal and bulbar muscular atrophy," *Neurology* 42, Dec. 1992, pp. 2300-2302.

S. Igarashi et al., "Suppression of aggregate formation and apoptosis by transglutaminase inhibitors in cells expressing truncated DRPLA protein with an expanded polyglutamine stretch," *Nature Genetics*, vol. 18, Feb. 1998, pp. 111-117.

M. V. Karpuj et al., "Prolonged survival and decreased abnormal movements in transgenic model of Huntington disease, with administration of the transglutaminase inhibitor cystamine," *Nature Medicine*, vol. 8, No. 2, Feb. 2002, pp. 143-149.

P. Kazemi-Esfarjani et al., "Evidence for a repressive function of the long polyglutamine tract in the human androgen receptor: possible pathogenetic relevance for the (CAG)n-expanded neuronopathies," *Human Molecular Genetics*, vol. 4, No. 4, 1995, pp. 523-527.

J. A. Kemppainen et al, "Androgen Receptor Phosphorylation, Turnover, Nuclear Transport, and Transcriptional Activation," *Journal of Biological Chemistry*, vol. 267, No. 2, Jan. 1992, pp. 968-974.

W. R. Kennedy et al., "Progressive proximal spinal and bulbar muscular atrophy of late onset: A sex-linked recessive trait," *Neurology*, vol. 18, Jul. 1968, pp. 671-680.

I. A. Klement et al., "Ataxin-1 Nuclear Localization and Aggregation: Role in Polyglutamine-induced Disease in SCA1 Transgenic Mice," *Cell*, Vo. 95, Oct. 1998, pp. 41-53.

Y. Kobayashi et al., "Caspase-3 Cleaves the Expanded Androgen Receptor Protein of Spinal and Bulbar Muscular Atrophy in a Polyglutamine Repeat Length-Dependent Manner," *Biochemical and Biophysical Research Communications* 252, 1998, pp. 145-150.

Y. Kobayashi et al., "Chaperones Hsp70 and Hsp40 Suppress Aggregate Formation and Apoptosis in Cultured Neuronal Cells Expressing Truncated Androgen Receptor Protein with Expanded Polyglutamine Tract," *Journal of Biological Chemistry*, vol. 275, No. 12, Mar. 2000, pp. 8772-8778.

A. R. La Spada et al., "Androgen receptor gene mutations in X-linked spinal and bulbar muscular atrophy," *Nature* vol. 352, Jul. 1991, pp. 77-79.

A. R. La Spada et al., "Meiotic stability and genotype-phenotype correlation of the trinucleotide repeat in X-linked spinal and bulbar muscular atrophy," *Nature Genetics*, vol. 2, Dec. 1992, pp. 301-304.

A. R. La Spada et al., "Androgen receptor YAC transgenic mice carrying CAG 45 alleles show trinucleotide repeat instability," *Human Molecular Genetics*, vol. 7, No. 6, 1998, pp. 959-967.

The Leuprolide Study Group, "Leuprolide Versus Diethylstilbestrol for Metastatic Prostate Cancer," *New England Journal of Medicine*, vol. 311, No. 20, Nov. 1984, pp. 1281-1286.

M. Li et al., "Nuclear Inclusions of the Androgen Receptor Protein in Spinal and Bulbar Muscular Atrophy," *American Neurological Association*, Vo.l. 44, No. 2, Aug. 1998, pp. 249-254.

M. Li et al., "Nonneural Nuclear Inclusions of Androgen Receptor Protein in Spinal and Bulbar Muscular Atrophy," *American Journal of Pathology*, vol. 153, No. 3, Sep. 1998, pp. 695-701.

H. E. MacLean et al., "Defects of androgen receptor function: from sex reversal to motor neurone disease," *Molecular and Cellular Endocrinology* 112, 1995, pp. 133-141.

C. Mariotti et al., "Phenotypic manifestations associated with CAG-repeat expansion in the androgen receptor gene in male patients and heterozygous females: a clinical and molecular study of 30 families," *Neuromuscular Disorders* 10, 2000, pp. 391-397.

A McCampbell et al., "CREB-binding protein sequestration by expanded polyglutamine," *Human Molecular Genetics*, vol. 9, No. 14, 2000, pp. 2197-2202.

M. J. McPhaul et al., "Genetic Basis of Endocrine Disease 4: The Spectrum of Mutations in the Androgen Receptor Gene that Causes Androgen Resistance," *Journal of Clinical Endocrinology and Metabolism*, Vo. 76, No. 1, 1993, pp. 17-23.

D. E. Merry et al., "Toward a mouse model for spinal and bulbar muscular atrophy: effect of neuronal expression of androgen receptor in transgenic mice," *Am. J. Hum. Genet* 59 suppl., 1996, A271.

A. N. Mhatre et al., "Reduced transcriptional regulatory competence of the androgen receptor in X-linked spinal and bulbar muscular atrophy," *Nature Genetics*, vol. 5, Oct. 1993, pp. 184-188.

J. R. Morrison et al., "A mouse model of spinal bulbar muscular atrophy (SBMA)," *Am. J. Hum. Genet.* 67 suppl. 2, 2000, A51.

H Nakajima et al., "Transcriptional activation by the androgen receptor in X-linked spinal and bulbar muscular atrophy," Journal of the Neurological Sciences 142, 1996, pp. 12-16.

F. Neuschmid-Kaspar et al., "CAG-repeat expansion in androgen receptor in Kennedy's disease is not a loss of function mutation," *Molecular and Cellular Endocrinology* 117, 1996, pp. 149-156.

H. Niwa et al., "Efficient selection for high-expression transfectants with a novel eukaryotic vector," *Gene* 108, 1991, pp. 193-199.

F. C. Nucifora Jr. et al., "Interference by Huntingtin and Atrophin-1 with CBP-Mediated Transcription Leading to Cellular Toxicity," *Science*, vol. 291, Mar. 2001, pp. 2423-2428.

V. O. Ona et al., "Inhibition of caspase-1 slows disease progression in a mouse model of Huntington's disease," *Nature*, vol. 399, May 1999, pp. 263-267.

H. T. Orr et al., "Expansion of an unstable trinucleotide CAG repeat in spinocerebellar ataxia type 1," Nature Genetics, vol. 4, Jul. 1993, pp. 221-226.

H. L. Paulson, "Toward an Understanding of Polyglutamine Neurodegeneration," *Brain Pathology* 10, 2000, pp. 293-299.

M. F. Peters et al., "Nuclear Targeting of Mutant Huntingtin Increases Toxicity," *Molecular and Cellular Neuroscience* 14,1999, pp. 121-128.

D. C. Rubinsztein, "Lessons from animal models of Huntington's disease," *Trends in Genetics*, vol. 18, No. 4, Apr. 2002, pp. 202-209.

F. Saudou et al., "Huntingtin Acts in the Nucleus to Induce Apoptosis but Death Does Not Correlate with the Formation of Intranuclear Inclusions," *Cell*, vol. 95, Oct. 1998, pp. 55-66.

S. Simeoni et al., "Motoneuronal cell death is not correlated with aggregate formation of androgen receptors containing an elongated polyglutamine tract," Human Molecular Genetics, vol. 9, No. 1, 2000, pp. 133-144.

G. Sobue et al., "X-Linked Recessive Bulbospinal Neuronopathy: A Clinicopathological Study," *Brain* 112, 1989, pp. 209-232.

G. Sobue et al., "Subclinical phenotypic expressions in heterozygous females of X-linked recessive bulbospinal neuronopathy," *Journal of the Neurological Sciences*, 117, 1993, pp. 74-78.

D. L. Stenoien et al., "Polyglutamine-expanded androgen receptors form aggregates that sequester heat shock proteins, proteasome components and SRC-1, and are suppressed by the HDJ-2 chaperone," Human Molecular Genetics, vol. 8, No. 5, 1999, pp. 731-741.

J. S. Steffan et al., "The Huntington's disease protein interacts with p53 and CREB-binding protein and represses transcription," Proc. Natl. Acad. Sci. USA. vol. 97, No. 12, Jun. 2000, pp. 6763-6768.

J. S. Steffan et al., "Histone deacetylase inhibitors arrest polyglutamine-dependent neurodegeneration in *Drosophila*," *Nature*, vol. 413, Oct. 2001, pp. 739-743.

A. J. Syms et al., "Mechanism of Androgen-receptor Augmentation: Analysis of Receptor Synthesis and Degradation by the Density-Shift Technique," *Journal of Biological Chemistry*, vol. 260, No. 1, Jan. 1985, pp. 455-461.

F. Tanaka et al., "Tissue-Specific Somatic Mosaicism in Spinal and Bulbar Muscular Atrophy Is Dependent on CAG-Repeat Length and Androgen Receptor-Gene Expression Level," *Am. J. Hum. Genet.* 65, 1999, pp. 966-973.

S. Terao et al., "Age-related changes in human spinal ventral horn cells with special reference to the loss of small neurons in the intermediate zone: a quantitative analysis," *Acta Neuropathol. (Berl)*, 92, 1996, pp. 109-114.

Y. Trottier et al., "Polyglutamine expansion as a pathological epitope in Huntington's disease and four dominant cerebellar ataxias," *Nature,* vol. 378, Nov. 1995, pp. 403-406.

J. M. Warrick et al., "Suppression of polyglutamine-mediated neurodegeneration in *Drosophila* by the molecular chaperone HSP70," *Nature Genetics*, vol. 23, Dec. 1999, pp. 425-428.

A. Yamamoto et al., "Reversal of Neuropathology and Motor Dysfunction in a Conditional Model of Huntington's Disease," *Cell*, vol. 101, Mar. 2000, pp. 57-66.

Z-X Zhou et al., "The Androgen Receptor: An Overview," *Recent Progress in Hormone Research*, vol. 49, 1994, pp. 249-274.

Z-X Zhou et al., "Specificity of Ligand- Dependent Androgen Receptor Stabilization: Receptor Domain Interactions Influence Ligand Dissociation and Receptor Stability," *Molecular Endocrinology*, vol. 9, No. 2, 1995, pp. 208-218.

H. Y. Zoghbi et al., "Glutamine Repeats and Neurodegeneration," *Annu. Rev. Neurosci.* 23, 2000, pp. 217-247.

M. Katsuno et al., "Testosterone Reduction Prevents Phenotypic Expression in a Transgenic Mouse Model of Spinal and Bulbar Muscular Atrophy," Neuron, vol. 35, Aug. 2002, pp. 843-854.

H. Adachi et al., "Transgenic Mouse Model of Spinal and Bulbar Muscular Atrophy," *Society for Neuroscience Abstract Viewer and Itinerary Planner,* 2002, No. 597.15.

R. S. Darrington et al., "Protective effects of estrogens on polyglumtamine-expanded human androgen receptor aggregation," *Neuroscience Letters* 350, 2003, pp. 37-40.

M. Katsuno et al., "Leuprorelin rescues polyglutamine-dependent phenotypes in a transgenic mouse model of spinal and bulbar muscular atrophy," Nature Medicine, vol. 9, No. 6, Jun. 2003, pp. 768-773.

The Office Action mailed on Nov. 11, 2005 for the corresponding Japanese patent application No. 2004-528895 and its partial translation.

Morrison et al., "A mouse model of spinal bulbar muscular atrophy (SBMA)", American Journal of Human Genetics, vol. 67, No. 4 Supplement 2, Oct. 2000, p. 51, XP002365115. & 50th Annual Meeting of the American Society of Human Genetics; Philadelphia, Pennsylvania, USA; Oct. 2-7, 2000, ISSN: 0002-9297.

Walcott et al., "Trinucleotide Repeat Disease. The Androgen Receptor in Spinal and Bulbar Muscular Atrophy." Vitamins and Hormones, vol. 65, 2002, pp. 127-147, XP009060762, ISSN: 0083-6729.

Adachi et al., "Transgenic mice with an expanded CAG repeat controlled by the human AR promoter show polyglutamine nuclear inclusions and neuronal dysfunction without neuronal cell death", Human Molecular Genetics, vol. 10, No. 10, May 1, 2001, pp. 1039-1048, XP002365116, ISSN: 0964-6906.

Warnock et al., "Depressive Symptoms Associated with Gonadotropin-Releasing Hormone Agonists", Depression and Anxiety, 1998, vol. 7, No. 4, 1998, pp. 171-177, XP002365117, ISSN: 1091-4269.

MacLean et al., "Abnormal Androgen Receptor Binding Affinity in Subjects with Kennedy's Disease (Spinal and Bulbar Muscular Atrophy)", Journal of Clinical Endocrinology and Metabolism, vol. 80, No. 2, 1995, pp. 508-516, XP002365118, ISSN: 0021-972X.

Supplementary Partial European Search Report dated Jan. 30, 2006.

Craig A. Peters, M.D. et al.; *The Effect of Nafarelin Acetate, A Luteinizing-Hormone-Releasing Hormone Agonist, on Benign Prostatic Hyperplasia,* The New England Journal of Medicine, vol. 317, No. 10; Sep. 3, 1987, 599-604.

W. Brian Peeling; *Phase III Studies to Compare Goserelin (Zoladex) with Orchiectomy and with Diethylstilbestrol in Treatment of Prostatic Carcinoma;* Supplement to Urology, vol. XXXIll, No. 5; May 1989, 45-52.

David G. McLeod; *Hormonal Therapy: Historical Perspective to Future Directions;* Urology 61 (Supplement 2A), Feb. 2003, 3-7.

Cary A. Presant et al.; *Buserelin as Primary Therapy in Advanced Prostatic Carcinoma;* Cancer, No. 10; Nov. 15, 1985; 2416-2419.

Paul Chrisp et al.; Goserelin *A Review of its Pharmacodynamic and Pharmacokinetic Properties and Clinical Use in Sex Hormone-Related Conditions;* Drugs 41(2); 1991, 254-288.

Fujino, Tanpakushitsu Kakusan Koso, 45: 1114-1118, 2000. Abstract only.

Saito et al., Nippon Hinyokika Gakkai Zasshi, 92:682-693, 2001. Abstract only.

* cited by examiner

Fig. 8

Phenotypes of transgenic mice

| Line | Copy number | Onset of weight loss (weeks) | Onset of rotarod impairment (weeks) | Median life expectancy (days) | 1C2 staining |
|---|---|---|---|---|---|
| AR-97Q | | | | | |
| 2-6 | 1-3 | 6 / 16 | 9 / 18 | 66 / >210 | ++ / + |
| 4-6 | 1-3 | 4 / 12 | 8 / 15 | 110 / >210 | ++ / + |
| 7-8 | 1-3 | 8 / 16 | 9 / 21 | 132 / >210 | ++ / + |
| 3-7 | ND | 8 / - | - / - | >210 | ND |
| 8-5 | ND | 8 / - | - / - | >210 | ND |
| AR-24Q | | | | | |
| 5-5 | 5 | - / - | - / - | ND | - / - |
| 8-7 | 1-3 | - / - | - / - | ND | - / - |
| 12-13 | 1-3 | - / - | - / - | ND | ND |

Fig. 9

| Distribution of nuclear inclusions and diffuse nuclear staining with 1C2 | | | | | | |
|---|---|---|---|---|---|---|
| Tissue | Male | | | Female | | |
| | Nuclear inclusions (NIs) / diffuse nuclear staining (D) | | | Nuclear inclusions (NIs) / diffuse nuclear staining (D) | | |
| | Total NIs / D | Neuronal NIs / D | Glial NIs / D | Total NIs / D | Neuronal NIs / D | Glial NIs / D |
| Neuronal | | | | | | |
| Cerebral cortex | +/++ | +/++ | +/++ | --+/+ | --+/+ | --+/+ |
| Olfactory bulb | +--+/+++ | +--+/++ | +/++ | --+/+ | --+/+ | --+/+ |
| Basal ganglia | +/++ | +/++ | +/++ | --+/--+ | --+/--+ | --+/--+ |
| Cerebellum | +--+/++ | +/++ | +--+/++ | --+/+ | --+/+ | --+/+ |
| Pons | +/++ | +/++ | +/++ | --+/--+ | --+/--+ | --+/--+ |
| Ependyma | --+/--+ | --+/--+ | | --+/--+ | --+/--+ | |
| Spinal cord | ++--+++/+++ | ++/++--+++ | ++/+++--++++ | --+/+ | --+/+ | --+/+ |
| Dorsal root ganglia | --+/--+ | --+/--+ | --/-- | --+/--+ | --+/--+ | --/-- |
| Non-neuronal | | | | | | |
| Muscle | ++/+ | | | --+/--+ | | |
| Heart | ++/+ | | | --+/--+ | | |
| Pancreas | --+/--++ | | | --+/--+ | | |
| Eye | --+/--+ | | | --/-- | | |
| Lung | --+/--+ | | | --/-- | | |
| Kidney | --/-- | | | --/-- | | |
| Liver | --/-- | | | --/-- | | |
| Stomach | --/-- | | | --/-- | | |
| Intestine | --/-- | | | --/-- | | |
| Spleen | --/-- | | | --/-- | | |
| Thymus | --/-- | | | --/-- | | |
| Skin | --/-- | | | --/-- | | |
| Prostate | --/+ | | | | | |
| Testis | --/-- | | | | | |
| Ovary | | | | | | |

METHODS FOR TREATING SPINAL AND BULBAR MUSCULAR ATROPHY USING LHRH ANALOGS

This application is a Divisional of prior application Ser. No. 10/524,823, filed on Feb. 18, 2005 now abandoned, which is hereby incorporated by reference.

TECHNICAL FIELD

The present invention relates to a non-human animal in which gene modification was performed. More particularly, the present invention relates to a non-human animal showing symptoms and pathologic findings being characteristic of spinal and bulbar muscular atrophy and the use thereof, as well as a therapeutic agent and a treatment method for spinal and bulbar muscular atrophy.

BACKGROUND ART

Spinal and bulbar muscular atrophy (SBMA) is an X-linked recessive and late-onset slow progressive lower motor neuron disease (Sobue et al., 1989; and Kennedy et al., 1968). Major symptoms are lowering of muscular power (weakness) and muscular atrophy in proximal limbs as well as bulbar palsy. Sensory nerve involvement, mainly deep sense impairment, is also found. As concomitant symptoms, gynecomastia is found at high rate, and hepatic dysfunction, glucose tolerance disorder, hyperlipidemia, hypertension, and the like, are often found. Also feminized skin, testicular atrophy, infertility and impotence are sometimes found. Female carriers are usually asymptomatic, although some express tremor of fingers, muscle cramp, mild increase in CK value, etc. (Sobue et al., 1993). A specific treatment for SBMA has not been established. Testosterone may be used as a symptomatic treatment, however, its effect is poor and the efficacy of long-term use has not been confirmed.

Pathologic conditions of SBMA include degeneration, or loss, of neurons in the ventral horn, facial nucleus and hypoglossal nucleus, which is caused by the abnormal expansion of CAG repeat in the first exon of the androgen receptor (AR) (La Spada et al., 1991). Normal number of the CAG repeats in AR gene is about 12 to 34, while that of SBMA patients is expanded to about 40 to 62. Therefore, SBMA is called polyglutamine disease along with Huntington's disease (HD), spinocerebellar ataxias, etc. These diseases share several pathologic conditions such as anticipation and variation in the number of CAG repeats (somatic mosaicism) (Tanaka et al., 1999), selective impairment of neuronal tissue. Furthermore) similar to the other polyglutamine diseases, SBMA also shows a negative correlation between the number of CAG repeats and age at onset of lowering of muscular power, and a positive correlation between the number of CAG repeats and the disease severity adjusted by age (Doyu et al., 1992).

Pathologically, nuclear inclusions stained with an anti-polyglutamine antibody and an anti-androgen receptor antibody are observed in the ventral horn, motor nucleus of lower cranial nerves, kidney, testis, skin, etc. (Li et al., 1998a; and Li et al., 1998b). Nuclear inclusion is among pathological characteristics of polyglutamine diseases and is thought to be involved in pathologic conditions of the disease (Zoghbi and Orr, 2000, and Paulson, 2000). However, the importance of nuclear inclusion in the pathophysiology of polyglutamine diseases has not been established. Some views that nuclear inclusion reflects a cellular protective mechanism for protecting the neuronal cell from the toxicity of the polyglutamine tract. On the other hand, many studies have suggested that, in almost all the polyglutamine diseases, nuclear translocation of mutant protein containing the polyglutamine tract is essential to the development of pathologic conditions (Klement et al., 1998, and Saudou et al., 1998). Unlike other polyglutamine diseases, SBMA is unique in that intracellular distribution of mutant protein changes due to the effect of the specific ligand. That is to say, it is known that AR, that is, a causative protein of SBMA, usually exists in cytoplasm as a complex in an inactivated state, and is transferred into the nucleus when it is bonded to testosterone that is a ligand (Zhou et al., 1994).

A toxic gain of function has been considered the main stream of the pathophysiology in polyQ diseases, but a loss of function of mutant proteins may also play a role (Zoghbi and Orr, 2000, Rubinsztein 2002). Although the expansion of polyQ tract in AR deteriorates the transcriptional activities of AR, and affects its interaction with other transcriptional factors and activators (Mhatre et al., 1993, Kazemi-Esfarjani et al., 1995, Chamberlain et al., 1994, Nakajima et al., 1996), the neurologic impairment in SBMA can not be attributed to the loss of AR function (Maclean et al., 1995, McPhaul et al., 1993), a reason why testosterone shows insufficient and transient effects when used as a therapeutic agent for SBMA (Danek et al., 1994, Goldenberg et al., 1996, Neuschmid-Kaspar et al., 1996).

There have been no substantially effective therapeutic approaches to the polyQ diseases. In a Tg mouse model of HD, expression of a dominant-negative caspase-1 mutant extended survival and delays the appearance of neuronal inclusions (Ona et al., 1999). Inhibition of mutant gene expression demonstrated the reversibility of phenotypic progression in a Tg mouse model of HD (Yamamoto et al., 2000). However, these gene modulations can not be directly applied clinically. Transglutaminase inhibitors suppressed aggregate formation and apoptosis in a cell model of DRPLA (Igarashi et al., 1998) and prolonged survival in a Tg mouse model of HD (Karpuj et al., 2002). An in vitro model of HD showed inhibition of huntingtin fibrillogenesis by specific antibodies and small molecules (Heiser et al., 2000). Creatine increased survival and delayed motor symptoms in a Tg mouse model of HD (Andreassen et al., 2001). Over-expression of molecular chaperone HSP70 demonstrated preventive effects in a *Drosophila* model of Machado-Joseph disease (Warrick et al., 1999) and SCA1 cell and Tg mouse models (Cummings et al., 1998, Cummings et al., 2001). HSP70 and HSP40 showed preventive effects also in a SBMA cell model (Kobayashi et al., 2000). These and other therapeutic approaches have, yet, remained insufficient or minimal in prevention of phenotypic expression and progression. Recently reported histone deacetylase inhibitors in a *Drosophila* model could be a promising candidate therapy for polyQ diseases (Steffan et al., 2001), but their therapeutic efficacy should be assessed in a Tg mouse model.

Meanwhile, generation of mouse models of SBMA and development of treatment method using the same have been attempted and some have been reported so far. Since no phenotypes were found in mice including a human androgen receptor gene (AR gene) having 45 or 66 CAG repeats, which are the same level as those of SBMA (Bingham et al., 1995, La Spada et al., 1998, and Merry et al., 1996), a Tg mouse having a truncated AR gene or a strong promoter have been developed for the purpose of obtaining mice showing symptoms. Mice expressing only 239CAG repeats under promoters of AR genes (Adachi et al., 2001) and mice in which a truncated AR gene having 112 CAG repeats is introduced (Abel et al., 2001) showed nuclear inclusions in the spinal motor neuron, in addition to symptoms such as motor weakness, weight loss, short life-span, etc.

As mentioned above, SBMA shows a remarkable sexual difference, that is, most patients are men and even if women have genetic abnormality, symptoms hardly appear. However, in the previous transgenic mice into which a truncated AR gene is introduced, such a sexual difference in symptoms is not observed (Adachi et al., 2001, and Abel et al., 2001). It is thought that no sexual difference in symptoms is found because transgenes of these mice do not have a full length and do not have the sequence encoding a biding site to ligand (testosterone). There was in the past only one SBMA Tg mouse model with a full-length human AR, which showed motor impairment, however, no significant sexual difference in symptoms has not been reported (Morrison et al., 2000).

SUMMARY OF THE INVENTION

The present invention was made on the basis of the above-mentioned background, and the final object of the present invention is to establish a treatment method for polyglutamine diseases (in particular, spinal and bulbar muscular atrophy). A specific problem thereof is to provide a model animal that faithfully reproduces pathologic conditions of human spinal and bulbar muscular atrophy, and to provide a screening method or an assessment method of a therapeutic agent for polyglutamine diseases using the model animal, as well as to provide a therapeutic agent and a treatment method for polyglutamine diseases.

The present inventors have investigated from the viewpoint of the above-mentioned problems, and succeeded in generating a transgenic mouse that faithfully reproduces the pathologic conditions of human spinal and bulbar muscular atrophy (SBMA). That is to say, firstly, the present inventors have attempted to generate a transgenic mouse (Tg mouse) by using a DNA construct containing a human androgen receptor (AR) gene having a CAG repeat sequence having 24 or 97 CAG repeats. When the present inventors have investigated symptoms and pathologic findings of the obtained Tg mouse, a Tg mouse having 97 CAG repeats faithfully reproduced the pathologic conditions of SBMA. In particular, unlike various kinds of SBMA model mice reported conventionally, this mouse model reproduces characteristics of human SBMA, that is, significant sexual difference in symptoms.

Then, various experiments using the Tg mice showed that when castration was performed to male mice so as to reduce the amount of circulating testosterone, symptoms and pathologic findings as shown in SBMA were remarkably improved. On the contrary, it was found that when testosterone was administered to female mice, symptoms, etc. as shown in SBMA were remarkably deteriorated. On the other hand, when an LHRH analog, having an effect of reducing luteinizing hormone-releasing hormone (LHRH) receptors of the pituitary gland, inhibiting the secretion of gonadotropin (LH, FSH, etc.) from the pituitary gland, and thereby inhibiting the secretion of testosterone, was administered to male Tg mice and the effect thereof was observed, similar to the case where the castration was performed, symptoms were remarkably improved. These results provide findings that reducing the circulating testosterone level is an effective means for the treatment of SBMA.

The present invention was completed based on the above results and provides the following configurations.
[1] A non-human animal comprising the following characteristics (1) to (5) in symptoms or pathologic findings:
  (1) showing progressive muscular atrophy;
  (2) showing lowering in muscular power;
  (3) showing diffuse nuclear staining and nuclear inclusions in immunostaining with the use of an anti-polyglutamine antibody;
  (4) showing diffuse nuclear staining and nuclear inclusions in immunostaining with the use of an anti-androgen receptor antibody; and
  (5) showing neurogenic change.
[2] A non-human animal described in [1], wherein when the animals are females, the above-mentioned (1) to (5) are not found or are found more slightly or mildly as compared with the case in male animals.
[3] A non-human animal described in [1] or [2], wherein the non-human animal is Rodentia.
[4] A non-human animal described in [1] or [2], wherein the non-human animal is a mouse.
[5] A method of screening therapeutic agents for polyglutamine diseases, the method comprising the following steps (a) and (b):
  (a) administering a test agent to the non-human animal described in any of [1] to [4]; and
  (b) examining whether or not at least one of the following (1) to (9) is improved in the non-human animal after the test agent was administered,
  (1) progressive muscular atrophy;
  (2) lowering in muscular power;
  (3) an amount of diffuse nuclear staining and nuclear inclusions found in immunostaining with the use of an anti-polyglutamine antibody;
  (4) an amount of diffuse nuclear staining and nuclear inclusions found in immunostaining with the use of an anti-androgen receptor antibody;
  (5) neurogenic change;
  (6) progressive motor impairment;
  (7) reduction in body size;
  (8) short life-span; and
  (9) reduced activity.
[6] A method for screening therapeutic agents for polyglutamine diseases, the method comprising the following steps (A) and (B):
  (A) administering a test agent to the non-human animal described in any of [1] to [4] and to the wild type thereof; and
  (B) comparing and assessing the level of at least one of the following (1) to (9) between the administered non-human animal and the wild type,
  (1) progressive muscular atrophy;
  (2) lowering in muscular power;
  (3) an amount of diffuse nuclear staining and nuclear inclusions found in immunostaining with an anti-polyglutamine antibody;
  (4) an amount of diffuse nuclear staining and nuclear inclusions found in immunostaining with an anti-androgen receptor antibody;
  (5) neurogenic change,
  (6) progressive motor impairment;
  (7) reduction in body size;
  (8) short life-span; and
  (9) reduced activity.
[7] The screening method described in [5] or [6], wherein the test agent is selected from compounds having an effect of inhibiting the secretion of testosterone.
[8] A therapeutic agent for polyglutamine diseases, comprising, as an active ingredient, the compound selected by the screening method described in any of [5] to [7].
[9] A therapeutic agent for spinal and bulbar muscular atrophy, comprising, as an active ingredient, a compound having an effect of inhibiting the secretion of testosterone.

[10] A therapeutic agent for spinal and bulbar muscular atrophy, comprising, as an active ingredient, a compound having an effect of inhibiting the secretion of gonadotropin from the pituitary gland.

[11] A therapeutic agent for spinal and bulbar muscular atrophy, comprising, as an active ingredient, a compound having an effect of reducing luteinizing hormone-releasing hormone receptors by acting on the pituitary gland.

[12] A therapeutic agent for spinal and bulbar muscular atrophy, comprising, as an active ingredient, an analog of luteinizing hormone-releasing hormone.

[13] A therapeutic agent for spinal and bulbar muscular atrophy, comprising, as an active ingredient, Leuprorelin or the derivative thereof.

BRIEF DESCRIPTION OF THE DRAWINGS

FIG. 8. Table summarizing the phenotypes of Tg mice generated in Examples. Each datum is expressed by male/female. In table, "−" indicates "not detected," "+" indicates "mild diffuse nuclear staining and nuclear inclusions are detected," "++" indicates "severe diffuse nuclear staining and nuclear inclusions are detected" and "ND" indicates "no data," respectively.

FIG. 9. Table summarizing the results of experiment using 1C2 antibody. In table, "−" indicates "not detected," "+" indicates "slightly detected," "++" indicates "moderately detected," and "+++" indicates "highly detected," respectively. When the findings are different between lines, the range of level is shown by using "-." Three lines of mice, #2-6, #4-6 and #7-8, are subjected to pathologic analysis at the age of 12, 18 and 15 week-old, respectively.

BEST MODE FOR CARRYING OUT THE INVENTION

Figure 1:
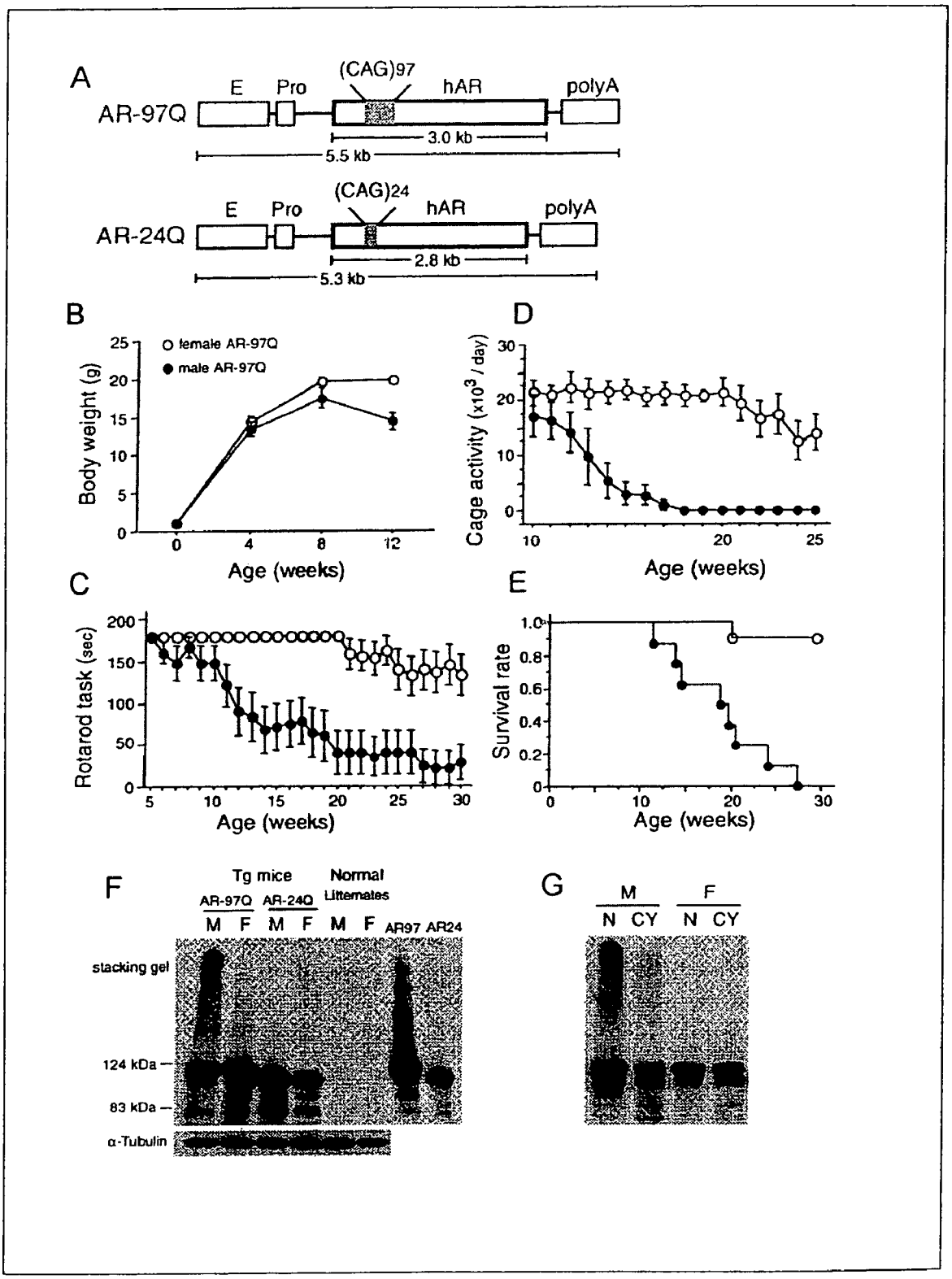
FIG. 1. Schematic structure of DNA constructs used in Examples, graph summarizing the results of experiment on symptoms of Tg mice, and graph summarizing the results of experiment on the expression of transgene. A. Schematic view of the transgene constructs. The DNA construct was composed of a cytomegalovirus enhancer (E), a chicken b-actin promoter (Pro), a full-length human AR containing 24 or 97 CAGs (hAR), and a rabbit β-globin polyadenylation signal sequence (polyA). B, C, D and E. Sexual differences in body weight (B, #2-6), rotarod task (C, #7-8), cage activity (D, #2-6), and survival rate (E, #7-8). All parameters are significantly different between the male mice (●, n=8) and female mice (○, n=8) ($p=0.001$, $p=0.003$, $p=0.005$, and $p=0.001$, respectively). F. Western blot analysis of total homogenates from the muscle of the male (M) and female (F) mice of AR-97Q, AR-24Q and normal littermates (12-week-old) immunolabeled by an antibody (N-20) against AR. Mouse AR was hardly detectable in the normal littermates. Comparison with muscle extracts from normal littermates indicated that most of the lower bands in transgenic (Tg) mice represent truncated human AR. Protein lysate from Neuro2a cells transfected with the transgene containing 24 CAGs and that with 97 CAGs (AR24 and AR97) are shown for size comparison. G. Western blot analysis of nuclear (N) and cytoplasmic (CY) fractions from the muscle of the male (M) and female (F) AR-97Q mice (#7-8,14-week-old) immunolabeled by N-20.

The first aspect of the present invention provides a non-human animal characterized by showing at least the following symptoms and pathologic findings.

The symptoms include (1) progressive muscular atrophy and (2) lowering in muscular power (weakness). Typically, as a result of or in relation to these symptoms, symptoms such as progressive motor impairment, reduction in body size, short life-span, and reduced activity, etc. are also found. Herein, the presence and level of progressive muscular atrophy can be confirmed, for example, by visually observing a certain site such as hind limbs and examining its change over time. On the other hand, the presence or level of lowering in muscular power can be confirmed indirectly from, for example, the presence or level of motor impairment or from the presence or level of reduced activity. Note here that the presence or level of motor impairment can be confirmed by, for example, Rotarod task test (Crawley J N. What's wrong with my mouse. Wiley-Liss, New York, Pp48-52.), and the presence or level of reduced activity can be confirmed by, for example, Cage activity test (Crawley J N. What's wrong with my mouse. Wiley-Liss, New York, Pp 48-52.), respectively. The other symptoms, that is, reduction in body size and short life-span can be confirmed by macroscopic examination or measurement of body weight for body size reduction and by examination of survival rate for short life-span, respectively.

One of the further features of the non-human animal of the present invention is significant sexual difference in symptoms. That is to say, the above-mentioned symptoms progress severely and rapidly in male mice, while not observed or far less severe in female mice as compared with the case of male mice. The difference in the symptoms related to such sexual difference is a feature specific to spinal and bulbar muscular atrophy. Thus, it can be said that the non-human animal of the present invention is extremely useful as a model animal of spinal and bulbar muscular atrophy because of such features.

In the non-human animal of the present invention, typically, as initial symptoms, muscle atrophy of the trunk and hind limbs is observed. Furthermore, typically, following these initial symptoms, weight loss and lowering in motor function are found.

The pathologic findings found in the non-human animal of the present invention include the following (3) to (5): (3) showing diffuse nuclear staining and nuclear inclusions in immunostaining with the use of an anti-polyglutamine antibody; (4) showing diffuse nuclear staining and nuclear inclusions in immunostaining with the use of an anti-androgen receptor antibody; and (5) showing neurogenic change. Herein, immunostaining can be carried out to the neuronal cell such as the spinal cord, cerebrum, cerebellum, etc. and non-neuronal tissue cells such as the muscle, heart and pancreas, etc. The non-human animal of the present invention shows the presence of such diffuse nuclear staining and nuclear inclusions from the age of about 4-week-old and the amount thereof increases according to aging. Note here that electron microscopic observation shows granular aggregates and fine microaggregates respectively corresponding to the above-mentioned diffuse nuclear staining and nuclear inclusions.

The neurogenic change can be confirmed by, for example, observing HE (hematoxylin-eosin) staining of the muscular tissue. Herein, the neurogenic change typically appears as the occurrence of grouped atrophy and small angulated fibers.

The non-human animal of the present invention shows remarkable sexual difference in pathologic findings as well as in the symptoms mentioned above. That is to say, the pathologic findings mentioned above are remarkably found in male mice, but not in female mice. Typically, neurogenic change, in particular, is not found in female mice.

The non-human animal of the present invention includes Rodentia such as mouse, rat, etc., but is not particularly limited thereto. The non-human animal of the present invention can be generated as a transgenic animal by inserting a certain gene into chromosome at the stage of generation. The method of generating transgenic animals may include a microinjection method of directly introducing DNA into the pronucleus of a fertilized egg, a method using a retrovirus vector, a method using ES cells, and the like. Hereinafter, as the method of generating the non-human animal of the present invention, the microinjection method using mice will be described as a specific example.

In the microinjection method, a fertilized egg is collected from the uterine tube of a female mouse, which was confirmed to be mated, and cultured. After culturing, a desired DNA construct is injected into the pronucleus. As the DNA construct, a sequence (which will be referred to as "transgene") encoding the full-length of a human androgen receptor (which will be also refereed to as "AR") containing a large number of CAG repeats is used. Herein, the number of CAG repeats needs to be sufficient for the generated transgenic mice to faithfully reproduce features of SBMA, and it is at least 40, preferably 70 or more, more preferably 80 or more, and yet further preferably 90 or more from the viewpoint that the number of CAG repeats in a SBMA patient is generally 40 or more. It is preferable that the DNA construct to be used includes a promoter sequence capable of efficiently expressing transgene. Examples of such a promoter may include a chicken β-actin promoter, a prion protein promoter, a human AR promoter, a neurofilament L-chain promoter, a L7 promoter, and a cytomegalovirus promoter, and the like.

A fertilized egg, which an injection operation was finished, is transplanted into the uterine tube of a pseudopregnant mouse and the transplanted mouse is cultured for a predetermine time so as to obtain a littermate mouse (FO). In order to confirm that transgene is appropriately introduced in the chromosome of the littermate mouse, DNA is extracted from the tail, etc. of the littermate mouse, and subjected to a PCR method using a primer specific to the transgene or a dot hybridization method, etc.

As mentioned above, the non-human animal of the present invention faithfully reproduces the features of spinal and bulbar muscular atrophy, however, most of the features are shared by polyglutamine diseases. Therefore, it is thought that the non-human animal of the present invention is useful for not only a model of spinal and bulbar muscular atrophy but also a model of a wide range of polyglutamine diseases. Therefore, the second aspect of the present invention provides a screening method of therapeutic agents for polyglutamine diseases using the non-human animal of the present invention.

The screening method of the present invention includes (a) a step of administering a test agent to the non-human animal according to the present invention, and (b) a step of examining whether or not symptoms or pathologic findings, which are characteristic of polyglutamine diseases, are improved in the non-human animal after the test agent was administered. In the step (b), when the improvement of the symptoms, etc. to be examined is found, it is determined that the test agent is a promising candidate of a therapeutic agent for polyglutamine diseases.

Note here that "therapeutic agent for polyglutamine diseases" is used as a term including not only agents to be used for the purpose of improving the symptoms of patients having polyglutamine disease but also agents to be used for the purpose of the prevention for individuals who might develop polyglutamine disease. Furthermore, in the present specification, "polyglutamine disease" is a general name of diseases characterized by the expansion of a CAG repeat in a coding region of the gene and includes Huntington's disease, spinocerebellar ataxias, and spinal and bulbar muscular atrophy, etc. Patients of polyglutamine disease share several pathologic conditions, for example, anticipation, variation in the number of CAG repeats (somatic mosaicism), as well as selective impairment of neuronal tissue.

Examples of administering a test agent in the step (a) may include oral, intravenous, intra-arterial, subcutaneous, intramuscular, intraperitoneal injection, or the like.

Examples of the test agent may include peptide, non-peptide low molecular weight compound, protein, glycoprotein, lipid, glycolipid, sugar, etc. They may be natural compounds or may be synthesized. Besides, extract, culture supernatant, or the like, of human cells or non-human animal cells, etc. may be used as the test agent.

When therapeutic agents for spinal and bulbar muscular atrophy among polyglutamine diseases are screened, it is preferable to select a test agent from compounds having an effect of inhibiting the secretion of testosterone. It is advantageous because efficient screening can be carried out. Examples of such compounds may include a compound having an effect of inhibiting the secretion of gonadotropin from the pituitary gland (for example, a compound having an effect of reducing a luteinizing hormone-releasing hormone receptor by acting on the pituitary gland). Further, a specific example of the test agent may include an analog of luteinizing hormone-releasing hormone or the derivative thereof.

The symptoms or pathologic findings being characteristic of the polyglutamine diseases in the step (b) include, for example, (1) progressive muscular atrophy, (2) lowering in muscular power (weakness), (3) an amount of diffuse nuclear staining and nuclear inclusions found in immunostaining with an anti-polyglutamine antibody, (4) an amount of diffuse nuclear staining and nuclear inclusions found in immunostaining with an anti-androgen receptor antibody, (5) neurogenic change, (6) progressive motor impairment, (7) reduction in body size, (8) short life-span; and (9) reduced activity. In the step (b), the change in at least one of the above (1) to (9) is examined. When a plurality of symptoms, etc. are examined, any symptoms may be combined arbitrarily. For example, combination of (1) and (2), combination of (1), (2) and (3), combination of (1), (2), (3) and (4), combination of (1), (2) and (5), combination of (3), (4) and (9) may be employed. Since it is thought that the efficacy of a test agent is generally enhanced in accordance with the increase of symptoms, etc. to be improved, in the step (b), it is preferable to examine a larger number of symptoms mentioned above. However, a correlation between two symptoms, etc. is found, either symptom, etc. may be examined.

Preferably, in parallel with the administration of the test agent to the non-human animal of the present invention, the test agent is administered to a wild type non-human animal. Thus, after administration, the levels of symptoms, etc. being characteristic of polyglutamine diseases are compared and assessed between both animals. The use of wild type animals as a control for comparison in this way enables easy and precise comparison of the efficacies of the test agent.

The compound selected by the screening method of the present invention can be sufficiently expected to be used as a therapeutic agent for polyglutamine diseases. When the selected compound has a sufficient efficacy with respect to polyglutamine diseases, the intact compound can be used as an active ingredient of the therapeutic agent. On the contrary, when the selected compound does not have a sufficient efficacy, the compound can be used as an active ingredient after the efficacy of the compound is enhanced by providing a chemical modification to the compound. Of course, for the purpose of increasing further efficacy, similar modification may be also provided to the compound having sufficient efficacy.

The third aspect of the present invention relates to an agent for spinal and bulbar muscular atrophy and comprises a compound having an effect of inhibiting the secretion of testosterone. Herein, the effect of inhibiting the secretion of testosterone may be obtained as a result of the administration of the agent of the present invention but the agent of the present invention may not directly have the effect. Therefore, the agent of the present invention may include, for example, a component having an effect of inhibiting the secretion of gonadotropin from the pituitary gland so as to inhibit the release of testosterone by gonadotropin, resulting in reducing the secretion amount of testosterone. Examples of such a component includes a component having an effect of reducing the expression amount luteinizing hormone-releasing hormone (hereinafter, which will be referred to as "LHRH") receptor by, for example, acting on the pituitary gland. For example, an LHRH analog can reduce the amount of LHRH receptors of the pituitary gland by the continuous stimulation thereof. Therefore, as the active ingredient of the present invention, an LHRH analog can be used. Examples of the LHRH analog may include Leuprorelin, Goserelin, Buserelin, and Nafarelin, etc., but is not limited thereto. Note here that Leuprorelin is sold under the pharmaceutical product name of "LEUPLIN®" (general name of active ingredient: leuprorelin acetate) from Takeda Chemical Industries, Co., Ltd. Similarly, Goserelin is sold under the pharmaceutical product name of "ZOLADEX®" (general name of the active ingredient: goserelin acetate) from AstraZeneca PLC. Similarly, Buserelin is sold under the pharmaceutical product name of "SUPRECUR®" (general name of the active ingredient: buserelin acetate) from Aventis Pharma Ltd. Similarly, Nafarelin is sold under the pharmaceutical product name of "NASANYL®" (general name of the active ingredient: nafarelin acetate) from Monsanto Japan Limited.

Note here that various derivatives to which modification is provided to the LHRH analog may be used as the active ingredient of the present invention as long as the effect of the LHRH analog is not lost (also including the case of enhancing the effect).

The agent of the present invention can be formulated according to the usual methods. In formulation, other pharmaceutically acceptable ingredients (for example, carrier, vehicle, disintegrator, buffer, emulsifier, suspension, soothing agent, stabilizer, preservative, antiseptics, physiological salt solution, and the like) can be contained. An example of the vehicle may include lactose, starch, sorbitol, D-mannitol, sucrose, and the like. An example of the disintegrator may include starch, carboxymethyl cellulose, calcium carbonate, and the like. An example of the buffer may include phosphate, citrate, acetate, and the like. An example of the emulsifier may include gum Arabic, sodium alginate, tragacanth, and the like. An example of the suspension may include glyceryl monostearate, aluminium monostearate, methyl cellulose, carboxymethyl cellulose, hydroxymethyl cellulose, sodium lauryl sulfate, and the like. An example of the soothing agent may include benzyl alcohol, chlorobutanol, sorbitol, and the like. An example of the stabilizer may include propylene glycol, diethyline sulfite, ascorbic acid, and the like. An example of the preservative may include phenol, benzalkonium chloride, benzyl alcohol, chlorobutanol, methylparaben, and the like. An example of the antiseptics can include benzalkonium chloride, parahydroxy benzoate, chlorobutanol, and the like.

Formulation forms are not particularly limited and may be formulated in a form of, for example, tablets, powder, fine granules, granules, capsules, syrup, injections, topical preparation, and suppository, and the like.

The thus formulated therapeutic agents of the present invention can be administered to patients by oral administration or parenteral administration (intravenous, intra-arterial, subcutaneous, muscular, intraperitoneal injection, and the like).

A further aspect of the present invention provides a treatment method for spinal and bulbar muscular atrophy with the use of the above-mentioned agents. The treatment method of the present invention includes a step of administering an agent containing, as an active ingredient, a compound having an effect of inhibiting the secretion of testosterone, to the living body. As mentioned above, "a compound having an effect of inhibiting the secretion of testosterone" herein is, for example, a compound having an effect of inhibiting the secretion of gonadotropin from the pituitary gland (for example, a compound acting on the pituitary gland so as to reduce the amount of LHRH receptors). Specific examples may include Leuprorelin, Goserelin, Buserelin, Nafarelin, etc., which are known as LHRH analogs, or the derivatives thereof.

The dosage amount of the agents differs depending upon symptoms, and age, sex, body weight of patients, and the like. The person skilled in the art can determine an appropriate dosage amount properly. For example, when an agent containing Leuprorelin as an active ingredient is used, it can be administrated to an adult subject so that the amount of Leuprorelin is about 1.5 to 4.0 mg/day (for example, 3.0 mg/day or 3.5 mg/day) every four weeks.

EXAMPLES

Each experiment in the below mentioned Examples is carried out by the following method unless otherwise noted.

(Transgene)

We generated DNA constructs including a human AR gene having CAG repeat sequence having 24 repeats (24CAG) or CAG repeat sequence having 97 repeats (97CAG) (SEQ ID NO: 1 and SEQ ID NO: 2 in this order) under the control of a chicken β-actin promoter (see FIG. 1A) as follows. pCAGGS vector (Niwa et al., 1991) was digested by HindIII and ligated after filling in, which generated the new NheI site (pCAGGS-NheI). The full-length human AR fragment harboring 24 or 97 CAGs (Kobayashi et al., 1998) were subcloned into pCAGGS-NheI. By direct DNA sequencing, the presence of 24 and 97 CAG repeat sequences was confirmed in the 5.3 and 5.5 kb-inserts respectively.

(Generation and Maintenance of Tg Mice)

The final plasmids with SalI-NheI were digested to remove the AR fragments. We generated Tg mice by microinjection into BDF1 fertilized eggs, and obtained 3 founders with AR-24Q and 5 founders with AR-97Q. These mice were backcrossed to C57BL/6J. We screened mouse tail DNA by PCR for the presence of the transgene using the primers 5'-CTTCTGGCGTGTGACCGGCG-3'(SEQ ID NO:3) and 5'-TGAGCTTGGCTGAATCTTCC-3'(SEQ ID NO:4) and the confirmation of the CAG repeat size using the primers 5'-CCAGAGCGTGCGCGAAGTG-3'(SEQ ID NO:5) and 5'-TGTGAAGGTTGCTGTTCCTC-3'(SEQ ID NO:6). The transgene copy number in each line was determined by densitometric comparison of Southern blot hybridization intensity of the AR DNA with known standards cutting only one site in the transgene using SacII. For determining CAG repeat size, we electrophoresed the PCR products amplified with a Texas Red-labeled primer on 6% denaturing polyacrylamide gel for 12 hours using a 5500 DNA sequencer (Hitachi, Japan).

(Neurological and Behavioral Testing)

We analyzed rotarod task of mice by an Economex Rotarod (Colombus Instruments, USA) weekly during the light phase of the 12 h light/12 h dark cycle as described previously (Adachi et al., 2001). We performed three trials, and recorded the longest duration on the rod for every mouse. We stopped the timer when the mouse fell from the rod or after an arbitrary limit of 180 seconds.

We measured cage activity while each mouse was in a transparent acrylic cage (16×30×14 cm). We used an AB system (Neuroscience, Japan) with an infrared ray sensor monitor to measure spontaneous motor activity. We automatically totaled and recorded all measurements for 24 hours per week at 10-min intervals.

(Hormonal Intervention and Serum Testosterone Assay)

Male AR-97Q mice and their normal littermates were castrated or sham-operated via the abdominal route under ketamine-xylazine anesthesia (50 mg/kg ketamine and 10 mg/kg xylazine, i.p.) at 4 weeks of age. Female AR-97Q mice and their littermates were subcutaneously injected 20 μg of testosterone enanthate dissolved in 20 μl of sesame oil weekly from 4 weeks of age until the end of the analysis. The control mice were given the same amount of sesame oil.

We used Coat-A-Count Total Testosterone radioimmunoassay (Diagnostic Products Corporation, USA) for assaying the serum testosterone levels.

(RNA and Protein Expression Analysis)

We exsanguinated mice under ketamine-xylazine anesthesia, snap-froze their tissues with powdered CO2 in acetone, extracted total RNA from tissues with Trizol (Life Technologies/Gibco BRL, USA), and reverse transcribed the RNA using SUPERSCRIPT II reverse transcriptase (Life Technologies/Gibco BRL). We used 5'-TTCCACACCCAGT-GAAGC-3' (SEQ ID NO:7) and 5'-GGCATTGGCCACAC-CAAGCC-3' (SEQ ID NO:8) as primers for specific transgene RNA detection. After amplification, the products were separated by agarose gel electrophoresis. We compared the intensity of the PCR products signals with those of β-actin mRNA levels, which were separately amplified, by ethidium bromide staining.

Frozen tissue (0.1 g wet weight) was homogenized in 1000 μl of 50 mM Tris pH 8.0, 150 mM NaCl, 1% NP-40, 0.5% deoxycholate, 0.1% SDS, and 1 mM 2-mercaptoethanol with 1 mM PMSF and aprotinine at 6 μg/ml (2500 g for 15 min at 4° C.). Each lane on a 5-20% SDS-PAGE gel was loaded with protein 200 μg for nervous tissue, and 80 μg for muscular tissue from the supernatant fraction, which was transferred to Hybond-P membranes (Amersham Pharmacia Biotech, England), using 25 mM Tris, 192 mM glycine, 0.1% SDS, and 10% methanol as transfer buffer. After immunoprobing with rabbit anti-AR antibody N-20 (1:1000) (Santa Cruz Biotechnology, USA), we performed second antibodyprobing and detection using the ECL+plus kit (Amersham Pharmacia Biotech). Nuclear and cytoplasmic fractions were extracted with NE-PER nuclear and cytoplasmic extraction reagents (Pierce, USA).

(Immunohistochemistry)

We perfused 20 ml of a 4% paraformaldehyde fixative in phosphate buffer (pH 7.4) through the left cardiac ventricle of mice deeply anesthetized with ketamine-xylazine, postfixed tissues overnight in 10% phosphate-buffered formalin, and processed tissues for paraffin embedding. Then we deparaffinized 4-μm-thick tissue sections, dehydrated with alcohol, treated in formic acid for 5 minutes at room temperature, and stained with 1C2 (1:10000) (Chemicon, USA), as described before (Adachi et al., 2001). That is to say, after treatment in formic acid, 5% equine serum was reacted at room temperature for 30 min, primary antibody 1C2 (1:10000) (Chemicon, USA) was reacted at 4° C. over night, followed by immunostaining by the ABC method. In the staining by the ABC method, a biotinylated secondary antibody (Vector Laboratories, USA) was reacted at 4° C. over night, washed with 0.02M PBS, reacted with HRP labeled streptavidin, and colored with DAB.

For electron microscopic immunohistochemistry, we used paraffin-embedded tissue sections immunostained with 1C2 (1:10000) (Chemicon) as described previously (Adachi et al., 2001).

(Muscle Histology and Morphometric Analysis of Spinal Motor Neurons and Ventral Spinal Roots)

Six-μm-thick cryostat sections of the gastrocnemius muscles were air dried and stained with hematoxylin and eosin (H & E). For assessment of the neuronal populations and cross-sectional area of the anterior horn cells, 20 serial 5-μm-thick sections from the fifth lumbar spinal cords of 3 mice of each group (#7-8,13-week-old) were prepared. Every other section was stained by the Nissl technique and all neurons with an obvious nucleolus, present in the anterior horn, were assessed using a Luzex FS image analyzer (Nireco, Japan) as described before (Terao et al., 1996). That is to say, the cross-sectional areas of total 10 sections of the entire neuron were measured. The diameter of myelinated fibers in the ventral spinal roots was measured on the transverse sections stained with toluidine blue as described before (Terao et al., 1996). That is to say, the cross-sectional area of each fiber was measured and the diameter of a circle having the same area was calculated.

(Statistical Analysis)

We analyzed data using the unpaired t-test and denoted p values of 0.05 or less as statistical significance.

Example 1

Generation of Transgenic Mice (Tg Mice) Expressing AR Gene Having 97CAGs and Investigation of Symptoms, Etc. of the Obtained Tg Mice We attempted to generate Tg mice expressing the full-length human AR containing 24 or 97 CAGs under the control of a cytomegalovirus enhancer and a chicken β-actin promoter (FIG. 1A). We established 3 lines with 24 glutamines (AR-24Q) and 5 lines with 97 glutamines (AR-97Q). Copy number of the transgene was 1 to 5 in AR-24Q mice, and 1 to 3 in AR-97Q mice (FIG. 8). We assessed the 24 or 97 CAG repeat in the transgene by the PCR amplification and the on the polyacrylamide gel electrophoresis. The results did not show unequivocal intergenerational instability in the CAG repeat number (data not shown).

Three of 5 lines with AR-97Q (#2-6, #4-6, #7-8) exhibited progressive motor impairment, although no lines with AR-24Q showed any manifested phenotypes. All 3 symptomatic lines showed reduction in body size, short life-span, progressive muscle atrophy and weakness as well as reduced cage activity; all of which were markedly pronounced and accelerated in the male AR-97Q mice, but not observed or far less severe in the female AR-97Q mice regardless of the line (FIGS. 1B, C, D and E). The first detectable phenotype is muscle atrophy of the trunk and hind limbs followed by weight loss and impairment of the rotarod task. We detected the onset of motor impairment by the rotarod task at 8 to 9 weeks of age in the male AR-97Q mice, while 16 weeks or more in the females (FIG. 8). The affected mice were hypoactive and dragged their hind limbs. The forelimbs were not involved until hind limb atrophy became severe. Males showed a markedly faster and earlier motor deficit than females, and shorter lifespan. The 50% mortality ranged from 66 to 135 days of age in the male AR-97Q mice of 3 lines, whereas mortality of the female AR-97Q mice remained only 10 to 30% at more than 210 days in the 3 lines. The cause of death was cachexia due to hyponutrition and dehydration.

Then, we examined the expression of transgene by the detection of protein by Western blot analysis and the detection of mRNA using RT-PCR method. As a result, Western blot analysis showed high expression of mutant AR, including mutant AR in the stacking gel and truncated mutant AR in addition to the mutant monomeric AR band. We detected these proteins in the spinal cord, cerebrum, heart, muscle and pancreas. Although the male mice had more protein within the stacking gel than the female mice, the female mice had more monomeric AR protein (FIG. 1F). AR-24Q mice showed a single band of AR with 24 glutamines without protein in the stacking gel (FIG. 1F). The nuclear fraction contained the most transgene protein within the stacking gel (FIG. 1G). There was no significant difference in the expression of the mRNA of the transgene between the male and female mice. These observations indicate that the nuclear localization is the major expression profile of the transgene protein in the stacking gel. This nuclear localization was more prominent in males than in females, while the mRNA expression levels were indistinguishable between genders.

On the other hand, we performed histological study including immunohistochemistry, as well as muscle histology and morphometric analysis of ventral horn cell and ventral root for each Tg mouse. AR-24Q mice showed no pathologic abnormalities. In AR-97Q mice, we detected diffuse nuclear staining and less frequent NIs with 1C2, an antibody specifically recognizing the expanded polyQ (Trottier et al., 1995), in the neurons of the spinal cord, cerebrum, cerebellum, brain stem and dorsal root ganglia as well as non-neuronal tissue such as the heart, muscle and pancreas (FIG. 9). In the neuronal tissues, the nuclei of the motor neurons showed the most prominent diffuse nuclear staining and NMs. Glial cells also showed marked staining but not the dorsal root ganglia. The regions with diffuse nuclear staining and NMs also showed immunoreactivity to an antibody to AR (N-20). Neither 1C2 nor N-20 revealed immunoreactivity in the cytoplasm. Diffuse nuclear staining and NMs were found at 4 weeks of age and became more profound with aging, although male mice showed markedly abundant diffuse nuclear staining and NMs than females in agreement with the symptomatic and western blot profile differences with gender (FIG. 9, FIG. 2A). Electron microscopic immunohistochemistry for 1C2 demonstrated granular aggregates corresponding to NIs and fine microaggregates corresponding to diffuse nuclear staining in the neuronal tissues (FIGS. 2B, C, D and E).

Figure 2:
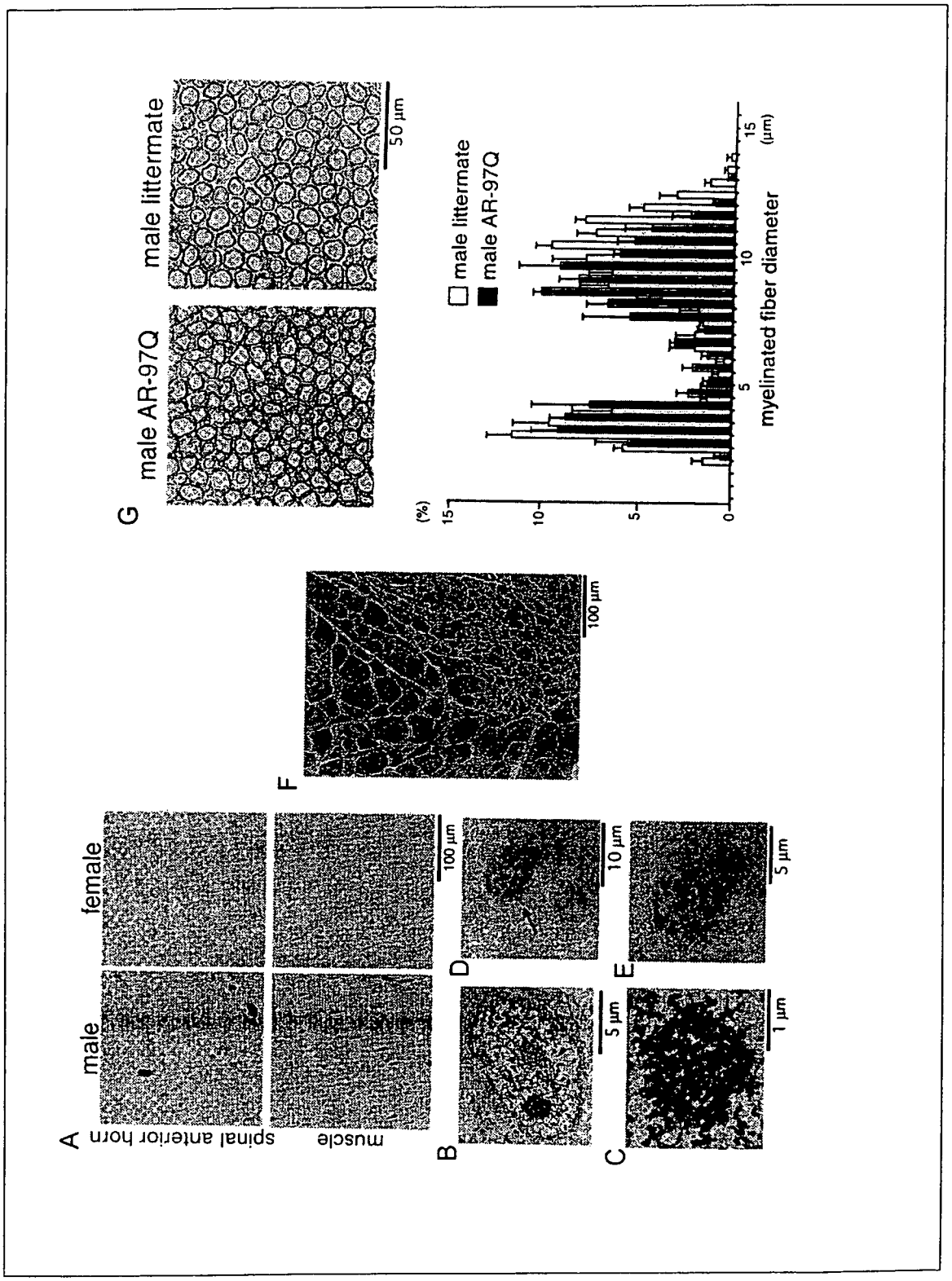
FIG. 2. Views summarizing pathologic findings of Tg mice. A. Immunohistochemical study of the male and female AR-97Q mice stained with a monoclonal antibody (1C2) against abnormally expanded polyglutamine (#7-8,14-week-old). B, C, C, D and E. Electron microscopic immunohistochemistry for 1C2 of an anterior horn cell (#4-6,24-week-old). Dense granular aggregate of 1C2-immunoreactive material was recognized in the motor neuron nucleus which showed a nuclear inclusion in light micrograph (B, low magnification and C, high magnification). Another motor neuron (D, arrow), which demonstrated diffuse nuclear staining in light micrograph, showed microaggregates in high magnification (E). F. HE staining of the muscle in the male AR-97Q mouse revealed obvious grouped atrophy and small angulated fibers. G. Toluidine blue staining and the histogram of myelinated fiber diameter of the L5 ventral root of male AR-97Q mice and their normal littermates. Large myelinated fibers in the ventral root showed axonal atrophy in the male AR-97Q mice (■, n=3) compared with normal littermates (□, n=3) (#7-8,13-week-old).

Muscle histology revealed significant grouped atrophy and small angulated fibers in the male AR-97Q mice as well as mild myopathic change such as increased variability in muscle fiber size (FIG. 2F). Although the number of spinal motor neurons tended to be reduced in AR-97Q mice, the difference was not significant; 452±10/10 sections in L5 segment of AR-97Q mice, and 543±28/10 sections in their littermates (p=0.10). Nevertheless, the cross-sectional area of the individual spinal motor neurons significantly decreased in the male AR-97Q mice; 195.6±12.1 $\mu m^2$ in L5 of male AR-97Q and 130.6±4.01 $\mu m^2$ in their male littermates (p=0.006). In addition, the diameter of large myelinated fibers (=6.0 $\mu m$) was significantly diminished in the male AR-97Q mice; the diameter of large fibers of the L5 ventral root was 8.49±0.27 $\mu m$ in male AR-97Q and 10.29±1.08 mm in their male littermates (p=0.05), whereas that of small fibers (<6.0 $\mu m$) was 3.11±0.23 $\mu m$ in male AR-97Q and 2.86±0.1 $\mu m$ in their male littermates (p=0.16). Female mice showed no neurogenic changes. Neuronal cell population in the cerebrum, cerebellum and dorsal root ganglia was fairly well preserved despite the abundant diffuse nuclear staining and NIs.

Example 2

Treatment of Male AR-97Q Mice by Castration

Figure 3:
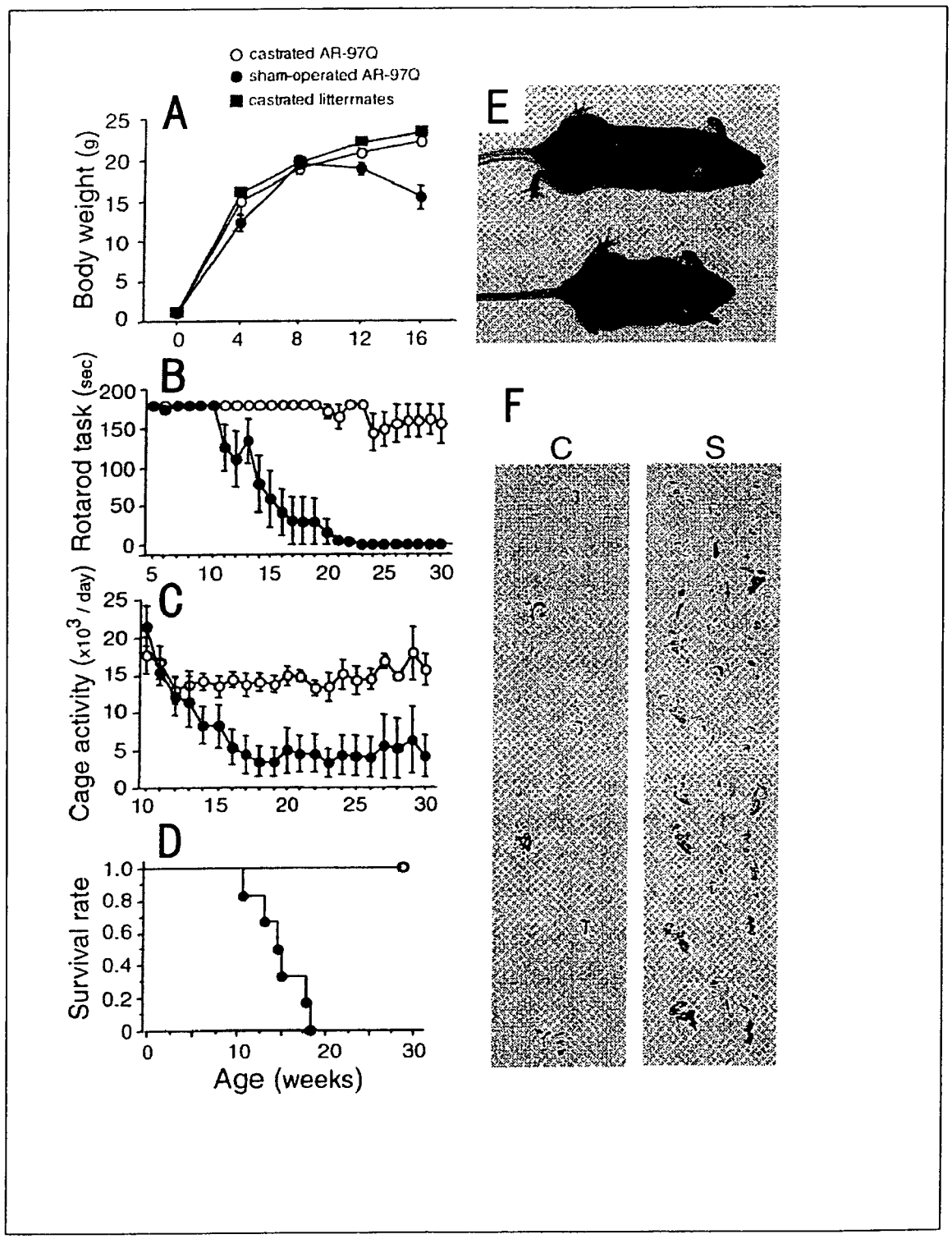
FIG. 3. Effects of castration on the symptomatic phenotypes of male AR-97Q mice. A, B, C, and D. Body weight (A, #7-8), rotarod task (B, #7-8), cage activity (C, #7-8), and survival rate (D, #2-6) of the castrated (○, n=6) and sham-operated (●, n=6) male AR-97Q mice. All parameters are significantly different between the sham-operated male AR-97Q mice and the castrated male AR-97Q mice or castrated male littermates (■, n=2) ($p=0.0001$, $p<0.0001$, $p=0.006$, and $p=0.0006$, respectively). E. The castrated AR-97Q mouse (E, top) shows no muscular atrophy, which is striking in control mouse (E, bottom) (#2-6,12-week-old). F. Foot prints of 12-week-old castrated (C) and control (S) male mice (#2-6). Front paws are in red, and hind paws in blue paint.
Figure 4:
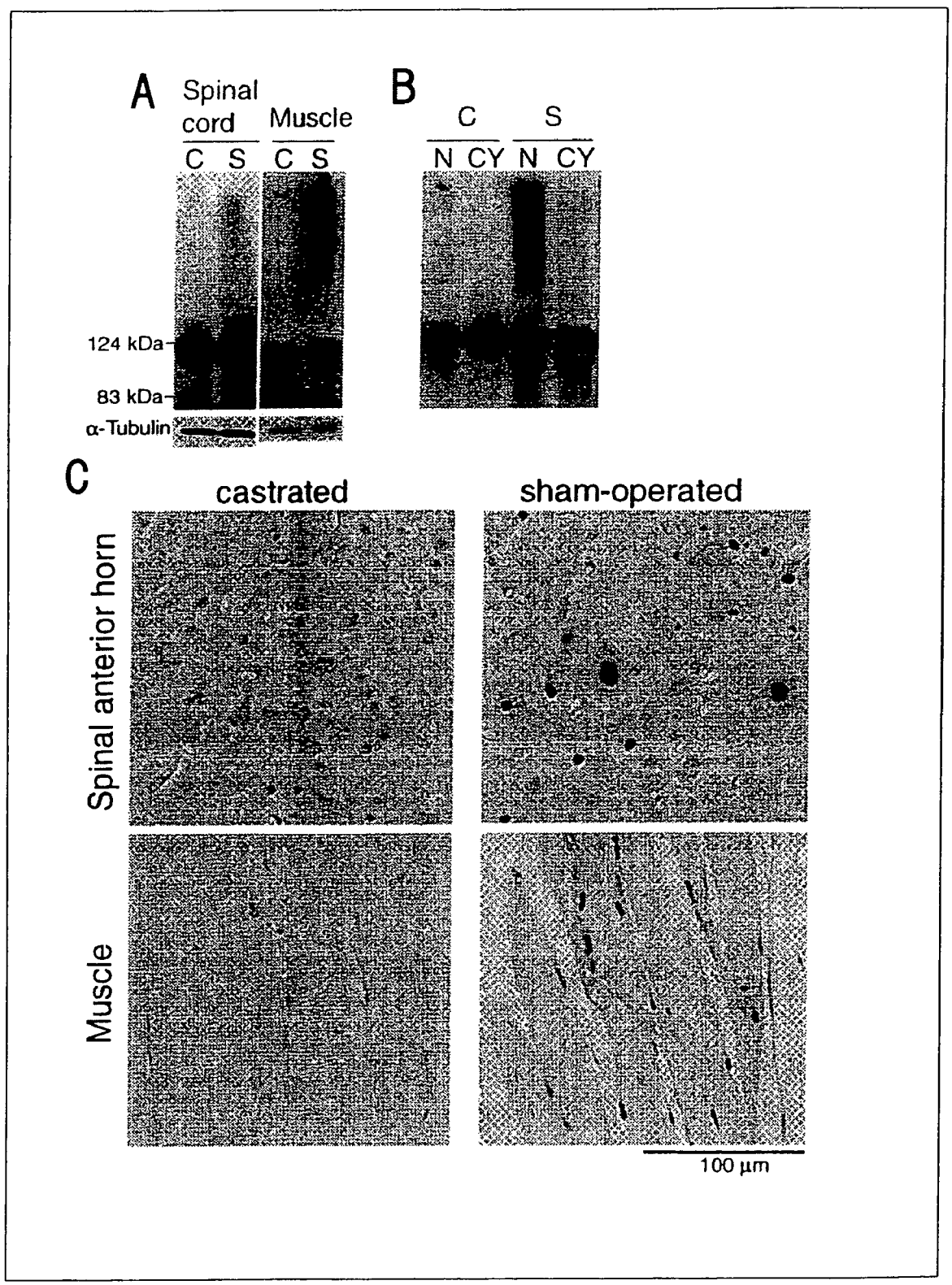
FIG. 4. Effects of castration on transgene expression and neuropathology of male AR-97Q mice. A. Western blot analysis of total homogenates from the spinal cord and muscle of the castrated (C) and control (S) male AR-97Q mice, that was immunolabeled by N-20 (#7-8,13-week-old). B. Western blot analysis of nuclear (N) and cytoplasmic (CY) fraction from the muscle of the castrated (C) and control (S) male AR-97Q mice, immunolabeled by N-20 (#7-8, 13-week-old). C. Immunohistochemical study using 1C2 showed marked differences of diffuse nuclear staining and nuclear inclusions between the castrated and sham-operated AR-97Q mice in the spinal anterior horn and the muscle (#7-8,13-week-old).

We hypothesized that sexual difference in symptoms and pathologic findings is caused by sexual difference of the secretion of testosterone that is androgen. Firstly, we performed castration treatment to male AR-97Q mice. Castrated male AR-97Q mice showed marked improvement of symptoms, pathologic findings, and nuclear localization of the mutant AR compared with control mice (the sham-operated male AR-97Q mice). These castrated male AR-97Q mice weighed the same as their castrated male littermates, whereas the sham-operated male AR-97Q mice showed progressive emaciation (FIG. 3A). Motor impairment assessed by rotarod and cage activity was significantly less or virtually absent in the castrated male AR-97Q mice as compared with control mice (FIGS. 3B and C). The castrated male AR-97Q mice showed motor impairment similar to that of the female AR-97Q mice. The life-span was also significantly prolonged in the castrated male AR-97Q mice (FIG. 3D). The castrated AR-97Q mice showed amelioration of muscle atrophy and reduction in body size (FIG. 3E). In a foot print analysis, the sham-operated male AR-97Q mice exhibited motor weakness with dragging of their hind legs, which improved in the castrated male AR-97Q mice (FIG. 3F). In the western blot analysis using N-20, the mutant AR appearing within the stacking gel was markedly diminished in the castrated male AR-97Q mice compared with the sham-operated male AR-97Q mice (FIG. 4A). The mutant AR in the nuclear fraction also significantly decreased in the castrated male AR-97Q mice (FIG. 4B). The castrated male AR-97Q mice showed markedly diminished diffuse nuclear staining and NIs (FIG. 4C). These observations suggested that castration markedly prevented nuclear localization of the mutant AR protein. The serum testosterone in the castrated male AR-97Q mice dramatically decreased to an undetectable low level, whereas that in sham-operated male AR-97Q mice was 27.7±1.2 ng/dl (#7-8, n=4).

Castration remarkably improved the phenotypes, i.e., symptoms and pathologic findings of male AR-97Q mice. Western blot analysis and 1C2 immunostaining revealed that castration drastically reduced the mutant ARs localized in nucleus. It was confirmed that castration reduced serum testosterone level. Since the nuclear translocation of AR is solely dependent on testosterone (Stenoien et al., 1999, and Simeoni et al., 2000), the reason why the castration shows the treatment effect in male mice is thought to be because castration prevented the nuclear localization of the mutant AR. The nuclear translocation of mutant protein having abnormally expanded polyglutamine is an important factor associated with neuronal dysfunction or degeneration in most of polyglutamine diseases. As one example, The nuclear localization of the mutant protein with expanded polyQ is important in inducing neuronal cell dysfunction and degeneration in the majority of polyQ diseases. Addition of a nuclear export signal to the mutant huntingtin eliminates aggregate formation and cell death in cell models of HD (Saudou et al., 1998, Peters et al., 1999), and a nuclear localization signal had the opposite effect (Peters et al., 1999). In Tg mice of SCA1 having a mutated nuclear localization signal, ataxin-1 was distributed in the cytoplasm, and the mice did not show any neurologic disorders (Klement et al., 1998). In considering such reports, it is thought that the nuclear translocation of mutant AR is prevented by reducing testosterone, which may lead to the improvement of symptoms of SBMA. Such endocrinologic intervention is thought to be sufficiently applicable to treatment of human.

The castrated AR-97Q mice showed phenotypes similar to those of the female AR-97Q mice, implying that motor impairment of SBMA patients can be rescued to the level in female carriers. Almost half of the human SBMA female carriers show mild subclinical electromyographic abnormalities, while few manifest clinical phenotypes (Sobue et al., 1993, Mariotti et al., 2000). Indeed lower expression level of mutant AR in female carriers due to X-inactivation may cause the escape from the manifestation, but our present study also suggests that the low level of testosterone prevents the nuclear localization of the expressed mutant AR, resulting in a lack of phenotypic manifestations in the female carriers.

Example 3

Administration of Leuprorelin to Male AR-97Q Mice

Figure 5:
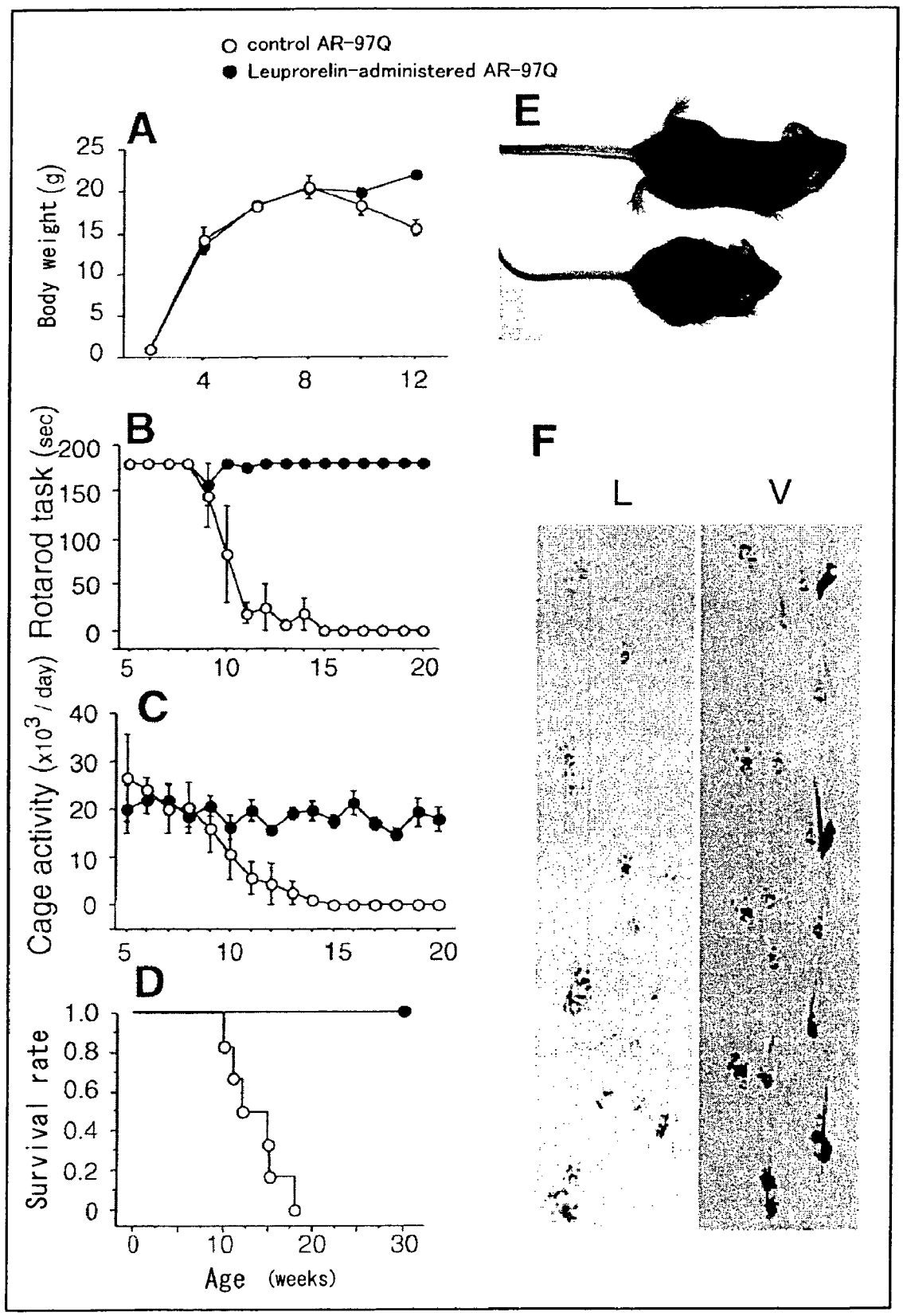
FIG. 5. Effects of Leuprorelin on the symptoms of male AR-97Q mice. A, B, C, and D. Body weight (A, #7-8), rotarod task (B, #7-8), cage activity (C, #7-8), and survival rate (D, #7-8) of Leuprorelin-administered and control (vehicle-administered) male AR-97Q mice. All parameters showed significant difference between the Leuprorelin-administered group (●, n=6) and the control group (○, n=6). The body size of the Leuprorelin-administered group (E, top) was normal, while that of the control group (E, bottom) showed severe muscular atrophy (#4-6, 12-week-old). F. Foot prints of 12-week-old Leuprorelin-administered (L) and control (V) male mice (#4-6). Front paws are in red, and hind paws in blue paint.

Then, we performed an experiment of administrating Lueprorelin, which is an LHRH analog, to male AR-97Q mice for the purpose of reproducing the treatment of mice by inhibiting the secretion of testosterone by the use of an agent. Leuprorelin was administrated as follows. 100 μg of Leuprorelin acetate was suspended in a solution containing D-mannitol, which was subcutaneously injected to the mice every two weeks from five weeks of age until the end of the analysis. To the control group, only suspension was administrated. The Leuprorelin-administered male AR-97Q mice showed remarkable improvement in symptoms as in castrated mice. That is to say, motor impairment assessed by rotarod and cage activity was far milder in the Leuprorelin-administrated male AR-97Q mice as compared with the control group, and motor dysfunction was hardly shown in the Leuprorelin-administrated group (FIGS. 5A, B, C and D). In Leuprorelin-administrated male AR-97Q mice, reduction in body size was remarkably improved (FIG. 5E) and also motor weakness was improved (FIG. 5F). Serum testosterone value of the Leuprorelin-administrated male AR-97Q mice was undetectable low level (#4-6, n=4).

Leuprorelin is an LHRH analog and is an agent that continuously stimulates the pituitary gland, thereby downregulating the LHRH receptor of the pituitary gland and inhibiting the secretion of LH or FSH from the pituitary gland so as to inhibit the secretion of testosterone. Leuprorelin shows the same level of effect of inhibiting the secretion of testosterone as that by castration (The Leuproride Study Group 1984), substitutes for highly invasive castration and becomes a representative agent for hormone treatment of prostate cancer. Furthermore, its long-lasting effect was confirmed and further the recovery of the secretion of testosterone by stopping the use was also confirmed (Hall et al., 1999). Also from the ethical viewpoint, this agent is suitable for clinical application. In the treatment of SBMA patients, administration of LHRH analog is thought to be more practical as compared with castration that is highly invasive and irreversible treatment. Also in AR-97Q mice, the effect of inhibiting the secretion of testosterone by Leuprorelin is obvious, and the treatment effect was shown also for neurologic impairment by polyglutamine. That is to say, LHRH analog is thought to be the most promising agent as a therapeutic agent for SBMA.

Example 4

Administration of Testosterone to Female AR-97Q Mice

Figure 6:
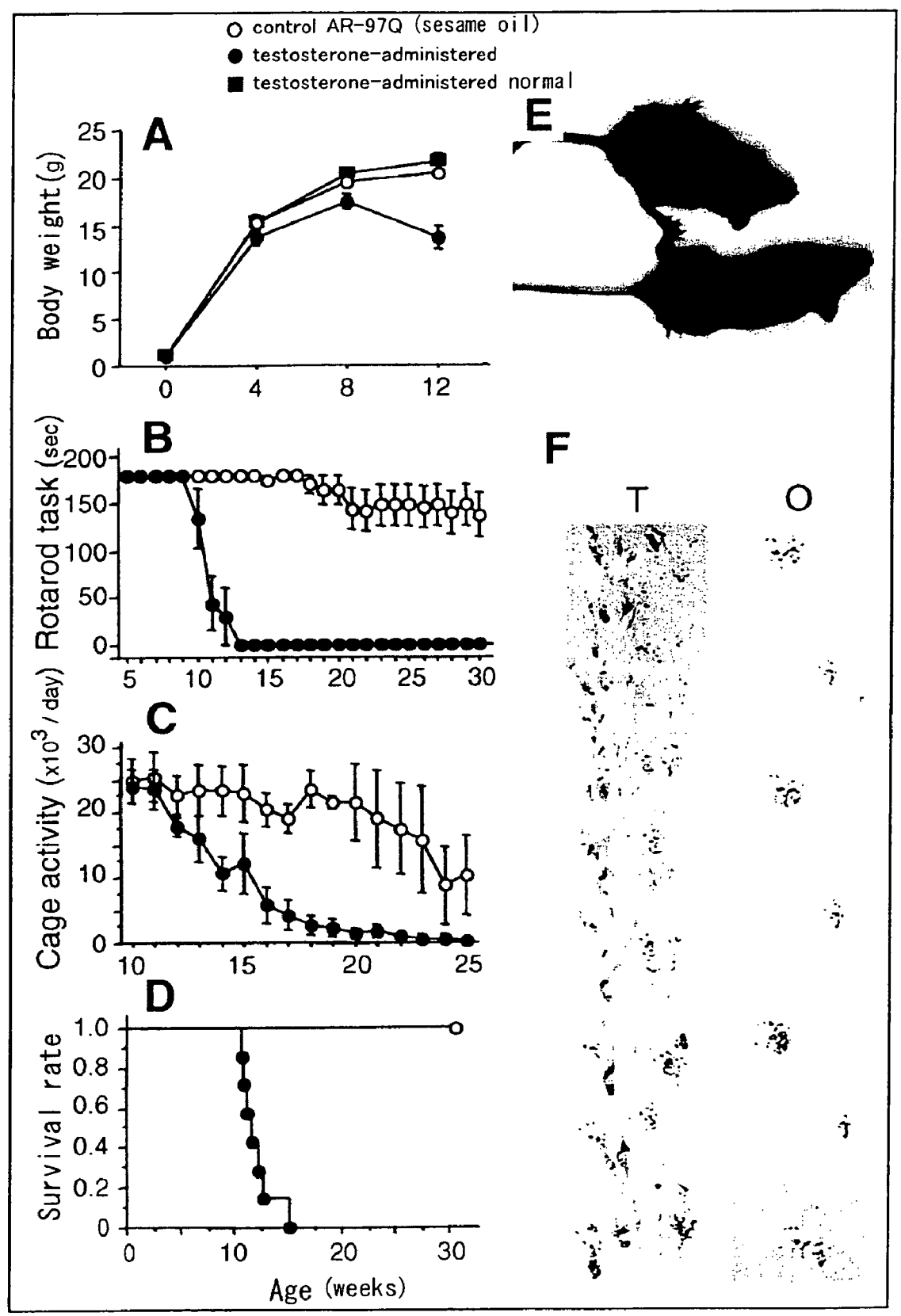
FIG. 6. Effects of testosterone on the symptoms of female AR-97Q mice. A, B, C, and D. Body weight (A, #7-8), rotarod task (B, #7-8), cage activity (C, #2-6), and survival rate (D, #7-8) of testosterone-administered and control (oil-administered) female AR-97Q mice. All parameters showed significant difference between the testosterone-administered group (●, n=6) and testosterone-administered normal mice (■, n=4), or the control group (0, n=6) ($p<0.0001$). The testosterone-administered AR-97Q mouse (E, top) showed severe muscular atrophy, but the body size of the control group (E, bottom) is normal (#2-6,14-week-old). F. Foot prints of 14-week-old testosterone-administered (T) and control (O) mice (#2-6). Front paws are in red, and hind paws in blue paint.
Figure 7:
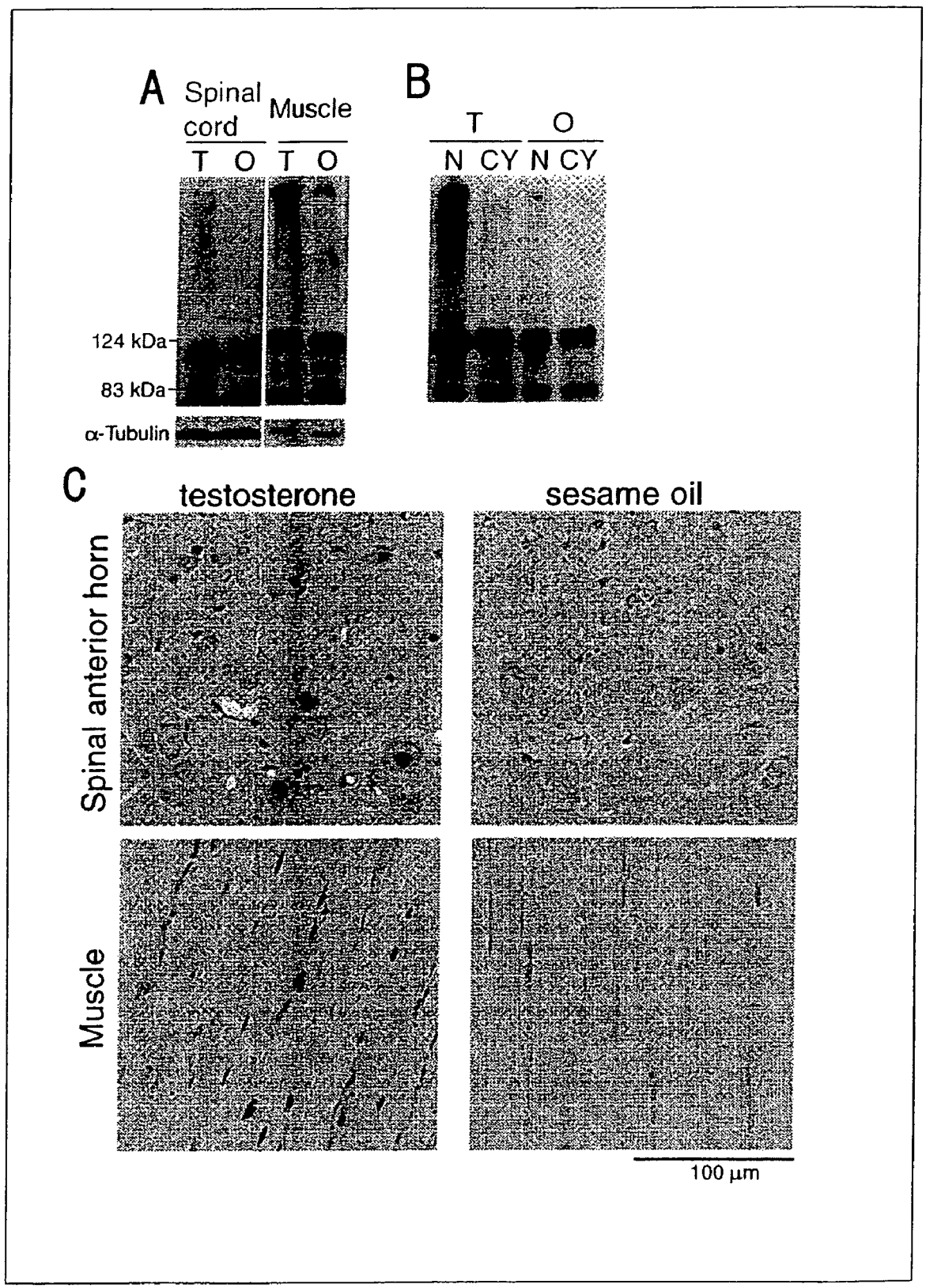
FIG. 7. Effects of testosterone on transgene expression and pathologic findings of male AR-97Q mice. A. The results of Western blot analysis of testosterone-administered group (T) and control group (O) using total homogenate of the spinal cord and muscle (#2-6,12-week-old). N-20 was used as an antibody. B. The results of Western blot analysis of nuclear (N) and cytoplasmic (Cy) fractions from the muscle of the testosterone administered group (T) and control group (O) (#2-6,12-week-old). N-20 was used as an antibody. Diffuse nuclear staining and nuclear inclusions found in immunostaining of the spinal cord and muscle by using 1C2 showed the remarkable difference between the testosterone-administered group and control group (C).

Then, in order to clarify that the treatment effect of castration in male AR-97Q mice is obtained by inhibiting the secretion of testosterone, we performed an experiment of administrating testosterone to female AR-97Q mice, which had originally shown less symptoms. Testosterone administration drastically exacerbated symptoms, pathologic findings and nuclear localization of the mutant protein in the female AR-97Q mice as compared with the control group (sesame-oil administrated group). That is to say, the control group hardly showed weight loss, while the testosterone-administrated mice showed significant weight loss (FIG. 6A). The motor impairment assessed by rotarod and cage activity was significantly worsened in the female AR-97Q mice administered testosterone compared with control mice, being similar to those of the untreated male AR-97Q mice (FIGS. 6B and C). The life-span of the female AR-97Q mice was also affected by testosterone administration (FIG. 6D). The testosterone-administered AR-97Q mice showed marked muscle atrophy and reduction in body size (FIG. 6E). In a foot print analysis, the testosterone-administered female AR-97Q mice exhibited motor weakness and dragged their hind legs, which was not detected in the sesame oil-administered female AR-97Q mice (FIG. 6F). Western blot analysis using N-20 revealed the mutant AR in the stacking gel in whole tissue homogenates as well as in the nuclear fraction, which was larger in amount in the testosterone-administered female AR-97Q mice than in control mice (FIGS. 7A and 7B). The testosterone-administered female AR-97Q mice demonstrated markedly pronounced diffuse nuclear staining and NIs with 1C2 compared with control mice (FIG. 7C). The testosterone-administered female 97Q mice showed markedly higher serum testosterone levels (158.0±70.7 ng/dl in #2-6, n=3; 305.3±182.3 ng/dl in #7-8, n=4) than those in control mice, all of which showed undetectable low level.

As is apparent from the above-mentioned results, administration of testosterone markedly exacerbated symptoms in the female AR-97Q mice, which had been negligible without testosterone treatment. Western blot analysis or 1C2 immunostaining revealed that the administration of testosterone markedly increased mutant AR localized in nucleus. It was confirmed that the administration of testosterone increased the serum testosterone level. Since the nuclear translocation of AR is solely dependent on testosterone (Stenoien et al., 1999, and Simeoni et al., 2000), testosterone may show toxic effects in the female AR-97Q mice by accelerating nuclear translocation of the mutant AR.

As shown in each Example, our Tg mice with the full-length human AR containing 97 CAGs demonstrated progressive motor impairment and neuropathologic changes equivalent to human SBMA. Western blot analysis showed truncated fragments of mutant AR in the affected tissues. These fragments may contribute to pathophysiology in our Tg mice, since several studies have suggested that proteolytic cleavage of mutant protein plays an important role in the pathogenic mechanisms of SBMA as well as other polyQ diseases (Li et al., 1998b, Kobayashi et al., 1998, Wellington et al., 1998, Mende-Mueller et al. 2001). Electron microscopic immunohistochemistry for 1C2 demonstrated granular aggregates and fine microaggregates, which indicates variable stages of pathologic change in the nucleus of motor neurons. Granular aggregate has also been reported in the pathologic study of SBMA (Li et al., 1998b). In AR-97Q mice in Examples, neurogenic changes were evident in muscle pathology, and anterior horn cells and their axons showed significant decrease in size without substantial neuronal loss. These findings indicate that the main pathologic features of our AR-97Q mice was neuronal dysfunction rather than degeneration of the spinal motor neurons, which was also demonstrated in a number of Tg mouse models of other polyQ diseases (Zoghbi and Orr, 2000, Rubinsztein, 2002). All symptomatic mice with AR-97Q showed motor impairment by 21 weeks of age, until when no lines with AR-24Q demonstrated symptoms in spite of the high revel expression of mutant AR protein. Nuclear inclusions and diffuse nuclear staining with 1C2 were found since 4 weeks of age even in female AR-97Q mice, although they are far less frequent than male AR-97Q mice. Nevertheless pathologic studies showed no abnormalities in AR-24Q mice at 12 weeks of age. These findings clarify that the symptomatic and pathologic phenotypes in AR-97Q were not due to overexpression of human AR but due to expanded polyglutamine tract. Moreover, no phenotypes were found in previous SBMA Tg mice with full length human AR despite good transgene expression levels, presumably because the CAG repeat was not long enough (Bingham et al, 1995, La Spada et al., 1998). In other words, the AR-97Q mouse faithfully reproduces pathologic conditions of SBMA and is thought to be an extremely excellent animal model of not only SBMA but also polyglutamine diseases.

The symptoms, pathologic findings and nuclear localization of the mutant AR protein showed a remarkable sexual difference in our AR-97Q mice, and were significantly modified by hormonal intervention either by castration, or Leuprorelin or testosterone administration. Although androgen has been shown to upregulate the expression of AR (Syms et al 1985, Kemppainen et al 1992, Zhou et al 1995), RT-PCR did not reveal any significant sexual difference in the mRNA levels of the transgenic AR gene in our Tg mice, in which the transgene was not controlled by its own promoter with androgen responsive element but by chicken β-actin promoter. That is to say, the mechanism that the testosterone level plays important roles in the sexual difference in symptoms is thought to be not changing the transcription of AR but modifying AR in the post-transcriptional stage, i.e., in the protein level.

Unlike SBMA, in the other polyglutamine diseases, specific ligand of the causative protein has not been found. The drastic effect of treatment by castration of Tg mice in the above-mentioned Examples suggests that polyglutamine diseases can be treated by inhibiting the nuclear translocation of mutant protein.

The present invention is not limited to the description of the above embodiments. A variety of modifications, which are within the scopes of the following claims and which are achieved easily by a person skilled in the art, are included in the present invention.

Document cited in the present description will listed below.

Abel, A., Walcott, J., Woods, J., Duda, J., and Merry, D. E. (2001). Expression of expanded repeat androgen receptor produces neurologic disease in transgenic mice. Hum. Mol. Genet. 10, 107-116.

Adachi, H., Kume, A., Li, M., Nakagomi, Y., Niwa, H., Do, J., Sang, C., Kobayashi, Y., Doyu, M., and Sobue, G. (2001). Transgenic mice with an expanded CAG repeat controlled by the human AR promoter show polyglutamine nuclear inclusions and neuronal dysfunction without neuronal cell death. Hum. Mol. Genet. 10, 1039-1048.

Andreassen, O. A., Dedeoglu, A., Ferrant.e, R. J., Jenkins, B. G., Ferrante, K. L., Thomas, M., Friedlich, A., Browne, S. E., Schilling, G., Borchelt, D. R., Hersch, S. M., Ross, C. A., and Beal, M. F. (2001). Creatine increase survival and delays motor symptoms in a transgenic animal model of Huntington's disease. Neurobiol. Dis. 8, 479-491.

Bingham P. M., Scott M. O., Wang S., McPhaul M. J., Wilson E. M., Garbem J. Y., Merry D. E., and Fischbeck K. H. (1995). Stability of an expanded trinucleotide repeat in the androgen receptor gene in transgenic mice. Nat. Genet. 9, 191-196.

Chamberlain, N. L., Driver, E. D., and Miesfeld, R. L. (1994). The length and location of CAG trinucleotide repeats in the androgen receptor N-terminal domain affect transactivation function. Nucleic Acids Res. 22, 31.81-3186.

Cummings, C. J, Mancini, M. A., Antalffy, B., DeFranco, D. B., Orr, H. T., and Zoghbi, H. Y. (1998). Chaperone suppression of aggregation and altered subcellular proteasome localization imply protein misfolding in SCA1. Nat. Genet. 19, 148-154.

Cummings, C. J., Reinstein, E., Sun, Y., Antalffy, B., Jiang, Y., Ciechanover, A., Orr, H. T., Beaudet, A. L., and Zoghbi, H. Y. (1999). Mutation of the E6-AP ubiquitin ligase reduces nuclear inclusion frequency while accelerating polyglutamine-induced pathology in SCA1 mice. Neuron 24, 879-892.

Cummings, C. J., Sun, Y., Opal, P., Antalffy, B., Mestril, R., Orr, H. T., Dillmann, W. H., and Zoghbi, H. Y. (2001). Overexpression of inducible HSP70 chaperone suppresses neuropathology and improves motor function in SCAL mice. Hum. Mol. Genet. 10, 1511-1518.

Danek, A., Witt, T. N., Mann, K., Schweikert, H. U., Romalo, G., La Spada, A. R., and Fischbeck, K. H. (1994). Decrease in androgen binding and effect of androgen treatment in a case of X-linked bulbospinal neuronopathy. Clin. Investig. 72, 892-897.

Doyu, M., Sobue, G., Mukai, E., Kachi, T., Yasuda, T., Mitsuma, T., and Takahashi, A. (1992). Severity of X-linked recessive bulbospinal neuronopathy correlates with size of the tandem CAG repeat in androgen receptor gene. Ann. Neurol. 32, 707-710.

Duyao, M., Ambrose, C., Myers, R., Novelletto, A., Persichetti, F., Frontali, M., Folstein, S., Ross, C., Franz, M., Abbott, M., Gray J., Conneally P., Young A., Penney J., Hollingsworth Z., Shoulson I., Lazzarini A., Falek A., Koroshetz W., Sax D., Bird E., Vonsattel J., Bonilla E., Alvir J., Conde J. B., Cha J-H., Dure L., Gomez F., Ramos M., Sanchez-Ramos J., Snodgrass S., de Young M., Wexler N., Moscowitz C., Penchaszadeh G., MacFarlane H., Anderson M., Jenkins B., Srinidhi J., Barnes G., Gusella J. and MacDonald M. (1993). Trinucleotide repeat length instability and age of onset in Huntington's disease. Nat. Genet. 4, 387-392.

Goldenberg, J. N., and Bradley, W. G. (1996). Testosterone therapy and the pathogenesis of Kennedy's disease (X-linked bulbospinal muscular atrophy). J. Neurol. Sci. 135, 158-161.

Gutekunst, C. A., Li, S. H., Yi, H., Mulroy, J. S., Kuemmerle, S., Jones, R., Rye, D., Ferrante, R. J., Hersch, S. M., and Li, X. J. (1999). Nuclear and neuropil aggregates in Huntington's disease: relationship to neuropathology. J. Neurosci. 19, 2522-2534.

Hall M. C., Fritzsch R. J., Sagalowsky A. I., Ahrens A., Petty B., and Roehrbom C. G. (1999). Prospective determination of the hormonal response after cessation of luteinizing hormone-releasing hormone agonist treatment in patients with prostate cancer. Urology 53: 898-902.

Heiser, V., Scherzinger, E., Boeddrich, A., Nordhoff, E., Lurz, R., Schugardt, N., Lehrach, H., and Wanker, E. E. (2000). Inhibition of huntingtin fibrillogenesis by specific antibodies and small molecules: implications for Huntington's disease therapy. Proc. Natl. Acad. Sci. USA. 97, 6739-6744.

Huynh D. P., Figueroa K., Hoang N., and Pulst S M. (2000). Nuclear localization or inclusion body formation of ataxin-2 are not necessary for SCA2 pathogenesis in mouse or human. Nat. Genet. 26, 44-50.

Igarashi, S., Tanno, Y., Onodera, O., Yamazaki, M., Sato, S., Ishikawa, A., Miyatani, N., Nagashima, M., Ishikawa, Y., Sahashi, K., Ibi, T., Miyatake, T., and Tsuji, S. (1992). Strong correlation between the number of CAG repeats in androgen receptor genes and the clinical onset of features of spinal and bulbar muscular atrophy. Neurology 42, 2300-2302.

Igarashi, S., Koide, R., Shimohata, T., Yamada, M., Hayashi, Y., Takano, H., Date, H., Oyake, M., Sato, T., Sato, A., Egawa, S., Ikeuchi, T., Tanaka, H., Nakano, R., Tanaka, K., Hozumi, I., Inuzuka, T., Takahashi, H., and Tsuj, S. (1998). Suppression of aggregate formation and apoptosis by transglutaminase inhibitors in cells expressing truncated DRPLA protein with an expanded polyglutamine stretch. Nat. Genet. 18, 111-117.

Karpuj M. V., Becher M. W., Springer J. E., Chabas D., Youssef S., Pedotti R., Mitchell D., and Steinman L. (2002). Prolonged survival and decreased abnormal movements in transgenic model of Huntington disease, with administration of the transglutaminase inhibitor cystamine. Nat. Med. 8, 143-149.

Kazemi-Esfarjani, P., Trifiro, M. A., and Pinsky, L. (1995). Evidence for a repressive function of the long polyglutamine tract in the human androgen receptor: possible pathogenetic relevance for the (CAG)n-expanded neuronopathies. Hum. Mol. Genet. 4, 523-527.

Kemppainen, J. A., Lane, M. V., Sar, M., and Wilson, E. M. (1992). Androgen receptor phosphorylation, turnover, nuclear transport and transcriptional activation. J. Biol. Chem. 267, 968-974.

Kennedy, W. R., Alter, M., and Sung, J. H. (1968). Progressive proximal spinal and bulbar muscular atrophy of late onset. A sex-linked recessive trait. Neurology 18: 671-80.

Klement, I. A., Skinner, P. J., Kaytor, M. D., Yi, H., Hersch, S. M., Clark, H. B., Zoghbi, H. Y., and Orr, H. T. (1998). Ataxin-1 nuclear localization and aggregation: role inpolyglutamine-induced disease in SCA1 transgenic mice. Cell 95, 41-53.

Kobayashi, Y., Miwa, S., Merry, D. E., Kume, A., Mei, L., Doyu, M., and Sobue, G. (1998). Caspase-3 cleaves the expanded androgen receptor protein of spinal and bulbar muscular atrophy in a polyglutamine repeat length-dependent manner. Biochem. Biophys. Res. Commun. 252, 145-150.

Kobayashi, Y., Kume, A., Li, M., Doyu, M., Hata, M., Ohtsuka, K., and Sobue, G. (2000). Chaperones Hsp70 and Hsp40 suppress aggregate formation and apoptosis in cultured neuronal cells expressing truncated androgen receptor protein with expanded polyglutamine tract. J. Biol. Chem. 275, 8772-8778.

La Spada, A. R., Wilson, E. M., Lubahn, D. B., Harding, A. E., and Fischbeck, K. H. (1991). Androgen receptor gene mutations in X-linked spinal and bulbar muscular atrophy. Nature 352, 77-79.

La Spada, A. R., Roling, D. B., Harding, A. E., Warner, C. L., Spiegel, R., Hausmanowa-Petrusewicz, I., Yee, W. C., and Fischbeck, K. H. (1992). Meiotic stability and genotype-phenotype correlation of the trinucleotide repeat in X-linked spinal and bulbar muscular atrophy. Nat. Genet. 2, 301-304.

La Spada A. R., Peterson K. R., Meadows S. A., McClain M. E., Jeng G., Chmelar R. S., Haugen H. A., Chen K., Singer M. J., Moore D., Trask B. J., Fischbeck K. H., Clegg C. H., and McKnight G. S. (1998). Androgen receptor YAC transgenic mice carrying CAG 45 alleles show trinucleotide repeat instability. Hum. Mol. Genet. 7, 959-967.

The Leuprolide Study Group (1984). Leuprolide versus diethylstilbestrol for metastatic prostate cancer. N. Engl. J. Med. 311: 1281-1286.

Li, M., Miwa, S., Kobayashi, Y., Merry, D. E., Yamamoto, M., Tanaka, F., Doyu, M., Hashizume, Y., Fischbeck, K. H., Sobue, G. (1998a). Nuclear inclusions of the androgen receptor protein in spinal and bulbar muscular atrophy. Ann. Neurol. 44, 249-254.

Li, M., Nakagomi, Y., Kobayashi, Y., Merry, D. E., Tanaka, F., Doyu, M., Mitsuma, T., Hashizume, Y., Fischbeck, K. H., and Sobue, G. (1998b). Normeural nuclear inclusions of androgen receptor protein in spinal and bulbar muscular atrophy. Am. J. Pathol. 153, 695-701.

MacLean, H. E., Warne, G. L., and Zajac, J. D. (1995). Defects of androgen receptor function: from sex reversal to motor neurone disease. Mol. Cell. Endocrinol. 112, 133-141.

Mariotti, C., Castellotti, B., Pareyson, D., Testa, D., Eoli, M., Antozzi, C., Silani, V., Marconi, R., Tezzon, F., Siciliano, G., Marchini, C., Gellera, C., and Donato, S. D. (2000). Phenotypic manifestations associated with CAG-repeat expansion in the androgen receptor gene in male patients and heterozygous females: a clinical and molecular study of 30 families. Neuromuscul. Disord. 10, 391-397.

McCampbell, A., Taylor, J. P., Taye, A. A., Robitschek, J., Li, M., Walcott, J., Merry, D., Chai, Y., Paulson, H., Sobue, G., and Fischbeck, K. H. (2000). CREB-binding protein sequestration by expanded polyglutamine. Hum. Mol. Genet. 9, 2197-2202.

McPhaul, M. J., Marcelli, M., Zoppi, S., Griffin, J. E., and Wilson, J. D. (1993). Genetic basis of endocrine disease. 4. The spectrum of mutations in the androgen receptor gene that causes androgen resistance. J. Clin. Endocrinol. Metab. 76, 17-23.

Merry D. E., McCampbell A., Taye A. A., Winston R. L. and Fischbeck K. H. (1996). Toward a mouse model for spinal and bulbar muscular atrophy: effect of neuronal expression of androgen receptor in transgenic mice. Am. J. Hum. Genet. 59 suppl., A271.

Mhatre, A. N., Trifiro, M. A., Kaufman, M, Kazemi-Esfarjani, P., Figlewicz, D., Rouleau, G., and Pinsky, L. (1993). Reduced transcriptional regulatory competence of the androgen receptor in X-linked spinal and bulbar muscular atrophy. Nat. Genet. 5, 184-188.

Morrison J. P., McManamny P., O'Bryan K. M., Cimdins K. L., Kola I., Cheema S., and deKretser D. M. (2000). A mouse model of spinal bulbar muscular atrophy (SBMA). Am. J. Hum. Genet. 67 suppl. 2, A51.

Nakajima, H., Kimura, F., Nakagawa, T., Furutama, D., Shinoda, K., Shimizu, A., and Ohsawa, N. (1996). Transcriptional activation by the androgen receptor in X-linked spinal and bulbar muscular atrophy. J. Neurol. Sci. 142, 12-16.

Neuschmid-Kaspar, F., Gast, A., Peterziel, H., Schneikert, J., Muigg, A., Ransmayr, G., Klocker, H., Bartsch, G., and Cato, A. C. (1996). CAG-repeat expansion in androgen receptor in Kennedy's disease is not a loss of function mutation. Mol. Cell. Endocrinol. 117, 149-156.

Niwa, H., Yamamura, K., and Miyazaki, J. (1991). Efficient selection for high-expression transfectants with a novel eukaryotic vector. Gene 108, 193-199.

Nucifora, F. C. Jr., Sasaki, M., Peters, M. F., Huang, H., Cooper, J. K., Yamada, M., Takahashi, H., Tsuji, S., Troncoso, J., Dawson, V. L., Dawson, T. M., and Ross, C. A. (2001). Interference by huntingtin and atrophin-1 with CBP-mediated transcription leading to cellular toxicity. Science 291, 2423-2428.

Ona V. O., Li M., Vonsattel J. P., Andrews L. J., Khan S. Q., Chung W. M., Frey A. S., Menon A. S., Li X. J., Stieg P. E., Yuan J., Penney J. B., Young A. B., Cha J. H., and Friedlander R. M. (1999). Inhibition of caspase-1 slows disease progression in a mouse model of Huntington's disease. Nature 399, 263-267.

Orr, H. T., Chung, M. Y., Banfi, S., Kwiatkowski, T. J. Jr., Servadio, A., Beaudet, A. L., McCall, A. E., Duvick, L. A., Ranum, L. P., and Zoghbi, H. Y. (1993). Expansion of an unstable trinucleotide CAG repeat in spinocerebellar ataxia type 1. Nat. Genet. 4, 221-226.

Paulson H L. (2000). Toward an understanding of polyglutamine neurodegeneration. Brain Pathol. 10, 293-299.

Peters, M. F., Nucifora, F. C. Jr., Kushi, J., Seaman, H. C., Cooper, J. K., Herring, W. J., Dawson, V. L., Dawson, T. M., and Ross, C. A. (1999). Nuclear targeting of mutant Huntingtin increases toxicity. Mol. Cell. Neurosci. 14, 121-128.

Rubinsztein D C. (2002). Lessons from animal models of Huntington's disease. Trends Genet. 18, 202-209.

Saudou, F., Finkbeiner, S., Devys, D., and Greenberg, M. E. (1998). Huntingtin acts in the nucleus to induce apoptosis but death does not correlate with the formation of intranuclear inclusions. Cell 95, 55-66.

Simeoni, S., Mancini, M. A., Stenoien, D. L., Marcelli, M., Weigel, N. L., Zanisi, M., Martini, L., and Poletti, A. (2000). Motoneuronal cell death is not correlated with aggregate formation of androgen receptors containing an elongated polyglutamine tract. Hum. Mol. Genet. 9, 133-144.

Sobue, G., Hashizume, Y., Mukai, E., Hirayama, M., Mitsuma, T., and Takahashi, A. (1989). X-linked recessive bulbospinal neuronopathy. A clinicopathological study. Brain 112, 209-232.

Sobue, G., Doyu, M., Kachi, T., Yasuda, T., Mukai, E., Kumagai, T., and Mitsuma, T. (1993). Subclinical phenotypic expressions in heterozygous females of X-linked recessive bulbospinal neuronopathy. J. Neurol. Sci. 117, 74-78.

Stenoien, D. L., Cummings, C. J., Adams, H. P., Mancini, M. G., Patel, K., DeMartino, G. N., Marcelli, M., Weigel, N. L., and Mancini, M. A. (1999). Polyglutamine-expanded androgen receptors form aggregates that sequester heat shock proteins, proteasome components and SRC-1, and are suppressed by the HDJ-2 chaperone. Hum. Mol. Genet. 8, 731-741.

Steffan, J. S., Kazantsev, A., Spasic-Boskovic, O., Greenwald, M., Zhu, Y. Z., Gohler, H., Wanker, E. E., Bates, G. P., Housman, D. E., and Thompson, L. M. (2000). The Huntington's disease protein interacts with p53 and CREB-binding protein and represses transcription. Proc. Natl. Acad. Sci. USA. 97, 6763-6768.

Steffan, J. S., Bodai, L., Pallos, J., Poelman, M., McCampbell, A., Apostol, B. L., Kazantsev, A., Schmidt, E., Zhu, Y. Z., Greenwald, M., Kurokawa, R., Housman, D. E., Jackson, G. R., Marsh, J. L., and Thompson, L. M. (2001). Histone deacetylase inhibitors arrest polyglutamine-dependent neurodegeneration in *Drosophila*. Nature 413, 739-743.

Syms, A. J., Norris, J. S., Panko, W. B., and Smith, R. G. (1985). Mechanism of androgen-receptor augmentation: analysis of receptor synthesis and degradation by the density-shift technique. J. Biol. Chem. 260, 455-461.

Tanaka, F., Reeves, M. F., Ito, Y., Matsumoto, M., Li, M., Miwa, S., Inukai, A., Yamamoto, M., Doyu, M., Yoshida, M., Hashizume, Y., Terao, S., Mitsuma, T., and Sobue, G. (1999). Tissue-specific somatic mosaicism in spinal and bulbar muscular atrophy is dependent on CAG-repeat length and androgen receptor—gene expression level. Am. J. Hum. Genet. 65, 966-973.

Terao S., Sobue G., Hashizume Y., Li M., Inagaki T., and Mitsuma T. (1996). Age-related changes in human spinal ventral horn cells with special reference to the loss of small neurons in the intermediate zone: a quantitative analysis. Acta Neuropathol. (Berl). 92, 109-114.

Trottier, Y., Lutz, Y., Stevanin, G., Imbert, G., Devys, D., Cancel, G., Saudou, F., Weber, C., David, G., Tora, L., Agid, Y., Brice, A., and Mandel, J-L. (1995). Polyglutamine expansion as a pathological epitope in Huntington's disease and four dominant cerebellar ataxias. Nature 378, 403-406.

Warrick, J. M., Chan, H. Y., Gray-Board, G. L., Chai, Y., Paulson, H. L., and Bonini, N. M. (1999). Suppression of polyglutamine-mediated neurodegeneration in *Drosophila* by the molecular chaperone HSP70. Nat. Genet. 23, 425-428.

Yamamoto, A., Lucas, J. J., and Hen R. (2000). Reversal of neuropathology and motor dysfunction in a conditional model of Huntington's disease. Cell 101, 57-66.

Zhou, Z. X., Wong, C. I., Sar, M., and Wilson, E. M. (1994). The androgen receptor: an overview. Recent Prog. Horm. Res. 49, 249-274.

Zhou, Z. X., Lane, M. V., Kemppainen, J. A., French, F. S., and Wilson, E. M. (1995). Specificity of ligand-dependent androgen receptor stabilization: receptor domain interactions influence ligand dissociation and receptor stability. Mol. Endocrinol. 9, 208-218.

Zoghbi, H. Y., and Orr, H. T. (2000). Glutamine repeats and neurodegeneration. Annu. Rev. Neurosci. 23, 217-247.

Hereinafter, the following matters are disclosed.

11. A non-human animal comprising the following (1) to (9) in symptoms or pathologic findings:
   (1) progressive muscular atrophy;
   (2) lowering in muscular power;
   (3) an amount of diffuse nuclear staining and nuclear inclusions found in immunostaining with an anti-polyglutamine antibody;
   (4) an amount of diffuse nuclear staining and nuclear inclusions found in immunostaining with an anti-androgen receptor antibody;
   (5) neurogenic change,
   (6) progressive motor impairment;
   (7) reduction in body size;
   (8) short life-span; and
   (9) reduced activity.

12. The non-human animal described in 11, wherein the motor impairment develops at the age of about 8 to 9 weeks.

13. The non-human animal described in 11 or 12, wherein when the animals are females, the above-mentioned (1) to (9) are not found or are formed more mildly or slightly as compared with the case of male animals.

14. The non-human animal described in any of 11 to 13, wherein the non-human animal is Rodentia.

15. The non-human animal described in any of 11 to 13, wherein the non-human animal is mouse.

21. A treatment method for spinal and bulbar muscular atrophy, comprising the following step (i):
   (i) administrating an agent containing, as an active ingredient, a compound having an effect of inhibiting the secretion of testosterone.

22. The treatment method described in 21, wherein the compound has an effect of inhibiting the secretion of gonadotropin from the pituitary gland.

23. The treatment method described in 21, wherein the compound has an effect of reducing luteinizing hormone-releasing hormone receptors by acting on the pituitary gland.

24. The treatment method described in 21, wherein the compound is an analog of luteinizing hormone-releasing hormone.

25. The treatment method described in 21, wherein the compound is Leuprorelin or the derivative thereof.

31. A use of a compound for producing a therapeutic agent for spinal and bulbar muscular atrophy, the compound having an effect of inhibiting the secretion of testosterone.

32. A use of a compound for producing a therapeutic agent for spinal and bulbar muscular atrophy, the compound having an effect of inhibiting the secretion of gonadotropin from the pituitary gland.

33. A use of a compound for producing a therapeutic agent for spinal and bulbar muscular atrophy, the compound having an effect of reducing luteinizing hormone-releasing hormone receptor by acting on the pituitary gland.

34. A use of analog of luteinizing hormone-releasing hormone for producing a therapeutic agent for spinal and bulbar muscular atrophy.

35. A use of Leuprorelin or the derivative thereof for producing a therapeutic agent for spinal and bulbar muscular atrophy.

INDUSTRIAL APPLICABILITY

The non-human animal of the present invention faithfully reproduces pathologic conditions of spinal and bulbar muscular atrophy (SBMA) and can be used as a model of SBMA for developing therapeutic agents and for elucidating the causative mechanism of SBMA, etc. Furthermore, the non-human animal of the present invention shows pathologic conditions shared by polyglutamine diseases, so that the animal can be used for developing therapeutic agents not only for SBMA but also for a wide range of polyglutamine diseases.

On the other hand, since the therapeutic agent of the present invention was formulated based on the development mechanism of SBMA and the effect was demonstrated in a model animal that faithfully reproduces pathologic conditions of SBMA, the agent is thought to be extremely useful as a therapeutic agent for SBMA.

The invention claimed is:

1. A method for treating spinal and bulbar muscular atrophy, comprising: administering, to a patient having spinal and bulbar muscular atrophy, a pharmaceutical composition consisting of an analog of luteinizing hormone-releasing hormone in a pharmaceutical acceptable carrier.

2. A method for treating spinal and bulbar muscular atrophy, comprising: administering, to a patient having spinal and bulbar muscular atrophy a pharmaceutical composition consisting of Leuprorelin or a derivative thereof in a pharmaceutical acceptable carrier.

3. The method of claim 2, wherein the Leuprorelin is administered at 1.5 to 4.0 mg/day every four weeks.

4. The method of claim 3, wherein the Leuprorelin is administered at 3.0 mg/day every four weeks.

5. The method of claim 3, wherein the Leuprorelin is administered at 3.5 mg/day every four weeks.

6. A method for treating spinal and bulbar muscular atrophy, consisting of: administering, to a patient having spinal and bulbar muscular atrophy, a pharmaceutical composition consisting of an analog of luteinizing hormone-releasing hormone in a pharmaceutical acceptable carrier.

* * * * *

SEQUENCE LISTING

<160> NUMBER OF SEQ ID NOS: 8

<210> SEQ ID NO 1
<211> LENGTH: 5285
<212> TYPE: DNA
<213> ORGANISM: Artificial Sequence
<220> FEATURE:
<223> OTHER INFORMATION: Description of Artificial Sequence:mutant
      human androgen receptor gene consisting 24 CAG repeats

<400> SEQUENCE: 1

| | | | | | | |
|---|---|---|---|---|---|---|
| tcgacattga | ttattgacta | gttattaata | gtaatcaatt | acggggtcat | tagttcatag | 60 |
| cccatatatg | gagttccgcg | ttacataact | tacggtaaat | ggcccgcctg | gctgaccgcc | 120 |
| caacgacccc | cgcccattga | cgtcaataat | gacgtatgtt | cccatagtaa | cgccaatagg | 180 |
| gactttccat | tgacgtcaat | gggtggacta | tttacggtaa | actgcccact | tggcagtaca | 240 |
| tcaagtgtat | catatgccaa | gtacgccccc | tattgacgtc | aatgacggta | aatggcccgc | 300 |
| ctggcattat | gcccagtaca | tgaccttatg | ggactttcct | acttggcagt | acatctacgt | 360 |
| attagtcatc | gctattacca | tgggtcgagg | tgagccccac | gttctgcttc | actctcccca | 420 |
| tctccccccc | ctccccaccc | ccaattttgt | atttatttat | tttttaatta | ttttgtgcag | 480 |
| cgatggggc | ggggggggg | ggggcgcgcg | ccaggcgggg | cggggcgggg | cgaggggcgg | 540 |
| ggcggggcga | ggcggagagg | tgcggcggca | gccaatcaga | gcggcgcgct | ccgaaagttt | 600 |
| ccttttatgg | cgaggcggcg | gcggcggcgg | ccctataaaa | agcgaagcgc | gcggcgggcg | 660 |
| ggagtcgctg | cgttgccttc | gccccgtgcc | ccgctccgcg | ccgcctcgcg | ccgcccgccc | 720 |
| cggctctgac | tgaccgcgtt | actcccacag | gtgagcgggc | gggacggccc | ttctcctccg | 780 |
| ggctgtaatt | agcgcttggt | ttaatgacgg | ctcgtttctt | ttctgtggct | gcgtgaaagc | 840 |
| cttaaagggc | tccgggaggg | ccctttgtgc | gggggggagc | ggctcggggg | gtgcgtgcgt | 900 |
| gtgtgtgtgc | gtggggagcg | ccgcgtgcgg | cccgcgctgc | ccggcggctg | tgagcgctgc | 960 |
| gggcgcggcg | cggggctttg | tgcgctccgc | gtgtgcgcga | ggggagcgcg | gccggggcg | 1020 |
| gtgccccgcg | gtgcgggggg | gctgcgaggg | gaacaaaggc | tgcgtgcggg | gtgtgtgcgt | 1080 |
| ggggggggtga | gcagggggtg | tgggcgcggc | ggtcgggctg | taaccccccc | ctgcaccccc | 1140 |
| ctccccgagt | tgctgagcac | ggcccggctt | cgggtgcggg | gctccgtgcg | gggcgtggcg | 1200 |
| cggggctcgc | cgtgccgggc | gggggtggc | ggcaggtggg | ggtgccgggc | ggggcggggc | 1260 |
| cgcctcgggc | cgggagggc | tcggggagg | ggcgcggcgg | ccccggagcg | ccggcggctg | 1320 |
| tcgaggcgcg | gcgagccgca | gccattgcct | tttatggtaa | tcgtgcgaga | gggcgcaggg | 1380 |
| acttcctttg | tcccaaatct | ggcggagccg | aaatctggga | ggcgccgccg | caccccctct | 1440 |
| agcgggcgcg | ggcgaagcgg | tgcggcgccg | gcaggaagga | aatgggcggg | agggccttc | 1500 |
| gtgcgtcgcc | gcgccgccgt | cccttctcc | atctccagcc | tcgggctgc | cgcaggggga | 1560 |
| cggctgcctt | cggggggac | ggggcagggc | ggggttcggc | ttctggcgtg | tgaccggcgg | 1620 |
| ctctagagcc | tctgctaacc | atgttcatgc | cttcttcttt | ttcctacagc | tcctgggcaa | 1680 |
| cgtgctggtt | attgtgctgt | ctcatcattt | tggcaaagaa | ttctagctgc | agcgactacc | 1740 |
| gcatcatcac | agcctgttga | actcttctga | gcaagagaag | gggaggcggg | gtaagggaag | 1800 |
| taggtggaag | attcagccaa | gctcaaggat | ggaagtgcag | ttagggctgg | gaagggtcta | 1860 |
| ccctcggccg | ccgtccaaga | cctaccgagg | agctttccag | aatctgttcc | agagcgtgcg | 1920 |

```
cgaagtgatc cagaacccgg gccccaggca cccagaggcc gcgagcgcag cacctcccgg    1980
cgccagtttg ctgctgctgc agcagcagca gcagcagcag cagcagcagc agcagcagca    2040
gcagcagcag cagcagcagc agcagcagca gcaagagact agcccaggc agcagcagca     2100
gcagcagggt gaggatggtt ctccccaagc ccatcgtaga ggccccacag gctacctggt    2160
cctggatgag gaacagcaac cttcacagcc gcagtcggcc ctggagtgcc accccgagag    2220
aggttgcgtc ccagagcctg gagccgccgt ggccgccagc aaggggctgc cgcagcagct    2280
gccagcacct ccggacgagg atgactcagc tgccccatcc acgttgtccc tgctgggccc    2340
cactttcccc ggcttaagca gctgctccgc tgaccttaaa gacatcctga gcgaggccag    2400
caccatgcaa ctccttcagc aacagcagca ggaagcagta tccgaaggca gcagcagcgg    2460
gagagcgagg gaggcctcgg gggctcccac ttcctccaag gacaattact taggggggcac   2520
ttcgaccatt tctgacaacg ccaaggagtt gtgtaaggca gtgtcggtgt ccatgggcct    2580
gggtgtggag gcgttggagc atctgagtcc aggggaacag cttcgggggg attgcatgta    2640
cgccccactt ttgggagttc cacccgctgt gcgtcccact ccttgtgccc cattggccga    2700
atgcaaaggt tctctgctag acgacagcgc aggcaagagc actgaagata ctgctgagta    2760
ttccccttc aagggaggtt acaccaaagg gctagaaggc gagagcctag gctgctctgg     2820
cagcgctgca gcagggagct ccgggacact tgaactgccg tctaccctgt ctctctacaa    2880
gtccggagca ctggacgagg cagctgcgta ccagagtcgc gactactaca actttccact    2940
ggctctggcc ggaccgccgc cccctccgcc gcctccccat ccccacgctc gcatcaagct    3000
ggagaacccg ctggactacg gcagcgcctg ggcggctgcg gcggcgcagt gccgctatgg    3060
ggacctggcg agcctgcatg gcgcgggtgc agcgggaccc ggttctgggt caccctcagc    3120
cgccgcttcc tcatcctggc acactctctt cacagccgaa gaaggccagt tgtatggacc    3180
gtgtggtggt ggtggggggtg gtggcggcgg cggcggcggc ggcggcggcg gcggcggcgg   3240
cggcggcggc ggcggcgagg cgggagctgt agccccctac ggctacactc ggccccctca    3300
ggggctggcg ggccaggaaa gcgacttcac cgcacctgat gtgtggtacc ctggcggcat    3360
ggtgagcaga gtgccctatc ccagtcccac ttgtgtcaaa agcgaaatgg gccccctggat  3420
ggatagctac tccggacctt acggggacat gcgtttggag actgccaggg accatgttt     3480
gcccattgac tattactttc cacccccagaa gacctgcctg atctgtggag atgaagcttc    3540
tgggtgtcac tatggagctc tcacatgtgg aagctgcaag gtcttcttca aaagagccgc    3600
tgaagggaaa cagaagtacc tgtgcgccag cagaaatgat tgcactattg ataaattccg    3660
aaggaaaaat tgtccatctt gtcgtcttcg gaaatgttat gaagcaggga tgactctggg    3720
agcccggaag ctgaagaaac ttggtaatct gaaactacag gaggaaggag aggcttccag    3780
caccaccagc cccactgagg agacaaccca gaagctgaca gtgtcacaca ttgaaggcta    3840
tgaatgtcag cccatctttc tgaatgtcct ggaagccatt gagccaggtg tagtgtgtgc    3900
tggacacgac aacaaccagc ccgactcctt tgcagccttg ctctctagcc tcaatgaact    3960
gggagagaga cagcttgtac acgtggtcaa gtgggccaag gccttgcctg gcttccgcaa    4020
cttacacgtg gacgaccaga tggctgtcat tcagtactcc tggatggggc tcatggtgtt    4080
tgccatgggc tggcgatcct tcaccaatgt caactccagg atgctctact cgcccctga    4140
tctggttttc aatgagtacc gcatgcacaa gtcccggatg tacagccagt gtgtccgaat    4200
gaggcacctc tctcaagagt ttggatggct ccaaatcacc ccccaggaat tcctgtgcat    4260
gaaagcactg ctactcttca gcattattcc agtggatggg ctgaaaaatc aaaaattctt    4320
```

```
tgatgaactt cgaatgaact acatcaagga actcgatcgt atcattgcat gcaaaagaaa    4380
aaatcccaca tcctgctcaa gacgcttcta ccagctcacc aagctcctgg actccgtgca    4440
gcctattgcg agagagctgc atcagttcac ttttgacctg ctaatcaagt cacacatggt    4500
gagcgtggac tttccggaaa tgatggcaga gatcatctct gtgcaagtgc ccaagatcct    4560
ttctgggaaa gtcaagccca tctatttcca cacccagtga agcattggaa accctatttc    4620
cccaccccag ctcatgcccc ctttcagatg tcttctgcct gttataactc tgcactactc    4680
ctctgcagtg ccttgggaa tttcctctat tgatgtacag tctgtcatgc tagaggatca     4740
attcactcct caggtgcagg ctgcctatca gaaggtggtg gctggtgtgg ccaatgccct    4800
ggctcacaaa taccactgag atctttttcc ctctgccaaa aattatgggg acatcatgaa    4860
gccccttgag catctgactt ctggctaata aaggaaattt attttcattg caatagtgtg    4920
ttggaatttt ttgtgtctct cactcggaag gacatatggg agggcaaatc atttaaaaca    4980
tcagaatgag tatttggttt agagtttggc aacatatgcc atatgctggc tgccatgaac    5040
aaaggtggct ataaagaggt catcagtata tgaaacagcc ccctgctgtc cattccttat    5100
tccatagaaa agccttgact tgaggttaga ttttttttat attttgtttt gtgttatttt    5160
tttctttaac atccctaaaa ttttccttac atgttttact agccagattt ttcctcctct    5220
cctgactact cccagtcata gctgtccctc ttctcttatg aagatccctc gacctgcagc    5280
ccaag                                                                5285

<210> SEQ ID NO 2
<211> LENGTH: 5505
<212> TYPE: DNA
<213> ORGANISM: Artificial Sequence
<220> FEATURE:
<223> OTHER INFORMATION: Description of Artificial Sequence:mutant
      human androgen receptor gene consisting 97 CAG repeats

<400> SEQUENCE: 2
gtcgacattg attattgact agttattaat agtaatcaat tacgggtca ttagttcata      60 gcccatatat ggagttccgc gttacataac ttacggtaaa tggcccgcct ggctgaccgc    120
ccaacgaccc ccgcccattg acgtcaataa tgacgtatgt tcccatagta acgccaatag    180
ggactttcca ttgacgtcaa tgggtggact atttacggta aactgcccac ttggcagtac    240
atcaagtgta tcatatgcca agtacgcccc ctattgacgt caatgacggt aaatggcccg    300
cctggcatta tgcccagtac atgaccttat gggactttcc tacttggcag tacatctacg    360
tattagtcat cgctattacc atgggtcgag gtgagcccca cgttctgctt cactctcccc    420
atctcccccc cctccccacc cccaattttg tatttattta ttttttaatt attttgtgca    480
gcgatggggg cggggggggg ggggcgcgc gccaggcggg gcgggcggg gcgaggggcg     540 gggcggggcg aggcggagag gtgcggcggc agccaatcag agcggcgcgc tccgaaagtt    600
tccttttatg gcgaggcggc ggcggcggcg gccctataaa aagcgaagcg cgcggcgggc    660
gggagtcgct gcgttgcctt cgccccgtgc ccgctccgc gccgcctcgc gccgcccgcc     720
ccggctctga ctgaccgcgt tactcccaca ggtgagcggg cgggacggcc cttctcctcc    780
gggctgtaat tagcgcttgg tttaatgacg gctcgtttct tttctgtggc tgcgtgaaag    840
ccttaaaggg ctccggagg gccctttgtg cggggggag cggctcgggg ggtgcgtgcg     900
tgtgtgtgtg cgtgggagc gccgcgtgcg gcccgcgctg cccggcggct gtgagcgctg    960
cgggcgcggc gcggggcttt gtgcgctccg cgtgtgcgcg aggggagcgc ggccggggc    1020
```

```
ggtgccccgc ggtgcggggg ggctgcgagg ggaacaaagg ctgcgtgcgg ggtgtgtgcg   1080
tgggggggtg agcagggggt gtgggcgcgg cggtcgggct gtaaccccccc cctgcacccc   1140 cctccccgag ttgctgagca cggcccggct tcggtgcgg ggctccgtgc ggggcgtggc   1200
gcggggctcg ccgtgccggg cggggggtgg cggcaggtgg gggtgccggg cggggcgggg   1260
ccgcctcggg ccggggaggg ctcggggag gggcgcggcg ccccggagc gccggcggct   1320 gtcgaggcgc ggcgagccgc agccattgcc ttttatggta atcgtgcgag agggcgcagg   1380
gacttccttt gtcccaaatc tggcggagcc gaaatctggg aggcgccgcc gcaccccctc   1440
tagcgggcgc gggcgaagcg gtgcggcgcc ggcaggaagg aaatgggcgg ggagggcctt   1500
cgtgcgtcgc cgcgccgccg tccccttctc catctccagc ctcggggctg ccgcaggggg   1560
acggctgcct tcgggggga cggggcaggg cggggttcgg cttctggcgt gtgaccggcg   1620
gctctagagc ctctgctaac catgttcatg ccttcttctt tttcctacag ctcctgggca   1680
acgtgctggt tattgtgctg tctcatcatt ttggcaaaga attctagctg cagcgactac   1740
cgcatcatca cagcctgttg aactcttctg agcaagagaa ggggaggcgg ggtaagggaa   1800
gtaggtggaa gattcagcca agctcaagga tggaagtgca gttagggctg ggaagggtct   1860
accctcggcc gccgtccaag acctaccgag gagcttttcca gaatctgttc cagagcgtgc   1920
gcgaagtgat ccagaacccg ggcccaggc acccagaggc cgcgagcgca gcacctcccg   1980
gcgccagttt gctgctgctg cagcagcagc agcagcagca gcagcagcag cagcagcagc   2040
agcagcagca gcagcagcag cagcagcagc agcagcagca gcagcagcag cagcagcagc   2100
agcagcagca gcagcagcag cagcagcagc agcagcagca gcagcagcag cagcagcagc   2160
agcagcagca gcagcagcag cagcagcagc agcagcagca gcagcagcag cagcagcagc   2220
agcagcagca gcagcagcag cagcagcagc agcagcagca gcagcagcag cagcagcagc   2280
agcagcagca gcaagagact agccccaggc agcagcagca gcagcaggt gaggatggtt   2340 ctccccaagc ccatcgtaga ggccccacag gctacctggt cctggatgag aacagcaac   2400 cttcacagcc gcagtcggcc ctggagtgcc accccgagag aggttgcgtc ccagagcctg   2460
gagccgccgt ggccgccagc aagggctgc cgcagcagct gccagcacct ccggacgagg   2520
atgactcagc tgccccatcc acgttgtccc tgctgggccc cactttcccc ggcttaagca   2580
gctgctccgc tgaccttaaa gacatcctga gcgaggccag caccatgcaa ctccttcagc   2640
aacagcagca ggaagcagta tccgaaggca gcagcagcgg gagagcgagg gaggcctcgg   2700
gggctcccac ttcctccaag gacaattact taggggggcac ttcgaccatt tctgacaacg   2760
ccaaggagtt gtgtaaggca gtgtcggtgt ccatggccct gggtgtggag gcgttggagc   2820
atctgagtcc agggaacag cttcgggggg attgcatgta cgccccactt ttgggagttc   2880
cacccgctgt gcgtcccact ccttgtgccc cattggccga atgcaaaggt tctctgctag   2940
acgacagcgc aggcaagagc actgaagata ctgctgagta ttcccctttc aagggaggtt   3000
acaccaaagg gctagaaggc gagagcctag gctgctctgg cagcgctgca gcagggagct   3060
ccgggacact tgaactgccg tctacccgtgt ctctctacaa gtccggagca ctggacgagg   3120
cagctgcgta ccagagtcgc gactactaca acttttccact ggctctggcc ggaccgccgc   3180
cccctccgcc gcctccccat ccccacgctc gcatcaagct ggagaacccg ctggactacg   3240
gcagcgcctg ggcggctgcg gcggcgcagt gccgctatgg ggacctggcg agcctgcatg   3300
gcgcgggtgc agcgggaccc ggttctgggt caccctcagc cgccgcttcc tcatcctggc   3360
```

```
acactctctt cacagccgaa gaaggccagt tgtatggacc gtgtggtggt ggtgggggtg    3420
gtggcggcgg cggcggcggc ggcggcggcg gcggcgcgg cggcggcggc ggcggcgagg    3480
cgggagctgt agcccctac ggctacactc ggcccctca ggggctggcg ggccaggaaa    3540
gcgacttcac cgcacctgat gtgtggtacc ctggcggcat ggtgagcaga gtgccctatc    3600
ccagtcccac ttgtgtcaaa agcgaaatgg gccctggat ggatagctac tccggacctt    3660
acggggacat gcgtttggag actgccaggg accatgtttt gcccattgac tattactttc    3720
caccccagaa gacctgcctg atctgtggag atgaagcttc tgggtgtcac tatggagctc    3780
tcacatgtgg aagctgcaag gtcttcttca aaagagccgc tgaagggaaa cagaagtacc    3840
tgtgcgccag cagaaatgat tgcactattg ataaattccg aaggaaaaat tgtccatctt    3900
gtcgtcttcg gaaatgttat gaagcaggga tgactctggg agcccggaag ctgaagaaac    3960
ttggtaatct gaaactacag gaggaaggag aggcttccag caccaccagc cccactgagg    4020
agacaaccca gaagctgaca gtgtcacaca ttgaaggcta tgaatgtcag cccatctttc    4080
tgaatgtcct ggaagccatt gagccaggtg tagtgtgtgc tggacacgac aacaaccagc    4140
ccgactcctt tgcagccttg ctctctagcc tcaatgaact gggagagaga cagcttgtac    4200
acgtggtcaa gtgggccaag gccttgcctg gcttccgcaa cttacacgtg gacgaccaga    4260
tggctgtcat tcagtactcc tggatggggc tcatggtgtt tgccatgggc tggcgatcct    4320
tcaccaatgt caactccagg atgctctact tcgcccctga tctggttttc aatgagtacc    4380
gcatgcacaa gtcccggatg tacagccagt gtgtccgaat gaggcacctc tctcaagagt    4440
ttggatggct ccaaatcacc ccccaggaat tcctgtgcat gaaagcactg ctactcttca    4500
gcattattcc agtggatggg ctgaaaaatc aaaaattctt tgatgaactt cgaatgaact    4560
acatcaagga actcgatcgt atcattgcat gcaaaagaaa aaatcccaca tcctgctcaa    4620
gacgcttcta ccagctcacc aagctcctgg actccgtgca gcctattgcg agagagctgc    4680
atcagttcac ttttgacctg ctaatcaagt cacacatggt gagcgtggac tttccggaaa    4740
tgatggcaga gatcatctct gtgcaagtgc ccaagatcct ttctgggaaa gtcaagccca    4800
tctatttcca cacccagtga agcattggaa accctatttc cccaccccag ctcatgcccc    4860
ctttcagatg tcttctgcct gttataactc tgcactactc ctctgcagtg ccttggggaa    4920
tttcctctat tgatgtacag tctgtcatgc tagaggatca attcactcct caggtgcagg    4980
ctgcctatca gaaggtggtg gctggtgtgg ccaatgccct ggctcacaaa taccactgag    5040
atctttttcc ctctgccaaa aattatgggg acatcatgaa gccccttgag catctgactt    5100
ctggctaata aaggaaattt attttcattg caatagtgtg ttggaattt ttgtgtctct    5160 cactcggaag acatatgggg agggcaaatc atttaaaaca tcagaatgag tatttggttt    5220
agagtttggc aacatatgcc atatgctggc tgccatgaac aaaggtggct ataagaggt    5280 catcagtata tgaaacagcc ccctgctgtc cattccttat tccatagaaa agccttgact    5340
tgaggttaga tttttttat attttgtttt gtgttatttt tttctttaac atccctaaaa    5400
ttttccttac atgttttact agccagattt ttcctcctct cctgactact cccagtcata    5460
gctgtccctc ttctcttatg aagatccctc gacctgcagc ccaag            5505
```

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence:primer for

```
                                    PCR

<400> SEQUENCE: 3
cttctggcgt gtgaccggcg                                                   20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence:primer for
      PCR

<400> SEQUENCE: 4
tgagcttggc tgaatcttcc                                                   20

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence:primer for
      PCR

<400> SEQUENCE: 5
ccagagcgtg cgcgaagtg                                                    19

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence:primer for
      PCR

<400> SEQUENCE: 6
tgtgaaggtt gctgttcctc                                                   20

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence:primer for
      RT-PCR

<400> SEQUENCE: 7
ttccacaccc agtgaagc                                                     18

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence:primer for
      RT-PCR

<400> SEQUENCE: 8
ggcattggcc acaccaagcc                                                   20
```